United States Patent [19]

Ladner

[11] Patent Number: 4,881,175

[45] Date of Patent: * Nov. 14, 1989

[54] COMPUTER BASED SYSTEM AND METHOD FOR DETERMINING AND DISPLAYING POSSIBLE CHEMICAL STRUCTURES FOR CONVERTING DOUBLE- OR MULTIPLE-CHAIN POLYPEPTIDES TO SINGLE-CHAIN POLYPEPTIDES

[75] Inventor: Robert C. Ladner, Iamsville, Md.

[73] Assignee: Genex Corporation, Gaithersburg, Md.

[*] Notice: The portion of the term of this patent subsequent to Nov. 3, 2004 has been disclaimed.

[21] Appl. No.: 204,940

[22] Filed: Jun. 9, 1988

Related U.S. Application Data

[63] Continuation of Ser. No. 115,919, Nov. 2, 1987, abandoned, which is a continuation of Ser. No. 902,970, Sep. 2, 1986, Pat. No. 4,704,692.

[51] Int. Cl.$^4$ .................. G06F 15/46; G01N 33/00
[52] U.S. Cl. .................. 364/496; 364/498; 436/86; 436/89
[58] Field of Search ............... 364/496–498, 364/413; 436/15, 43, 86–90

[56] References Cited

U.S. PATENT DOCUMENTS

| | | | |
|---|---|---|---|
| 4,085,443 | 4/1978 | DuBois et al. | 340/711 |
| 4,266,253 | 5/1981 | Matherat | 358/257 |
| 4,414,629 | 11/1983 | Waite | 364/300 |
| 4,704,692 | 11/1987 | Ladner | 364/496 |
| 4,719,582 | 1/1988 | Ishida et al. | 364/497 |

OTHER PUBLICATIONS

Small Business Innovation Phase I Grant Application of Creative BioMolecules, Inc., Aug. 1984.
Small Business Innovation Phase II Grant Application of Creative BioMolecules, Inc., Dec. 1985.

*Primary Examiner*—Parshotam S. Lall
*Assistant Examiner*—Brian M. Mattson
*Attorney, Agent, or Firm*—Saidman, Sterne, Kessler & Goldstein

[57] ABSTRACT

A computer based system and method determines and displays possible chemical structures for converting two naturally aggregated but chemically separated polypeptide chains into a single polypeptide chain which will fold into a three dimensional structure very similar to the original structure made of the two polypeptide chains. A data base contains a large number of amino acid sequences for which the three dimensional structure is known. After plausible sites have been selected, this data base is examined to find which amino acid sequences (linkers) can bridge the gap between the plausible sites to create a plausible one-polypeptide structure. The testing of each possible linker proceeds in three steps. First, the span (a scalar quantity) of the candidate is compared to the span of the gap. If the span is close enough, step two is done which involves aligning the first peptides of the candidate with the initial peptide of the gap. The three dimensional vector from tail to head of the candidate is compared to the three dimensional vector from tail to head of the gap. If there is a sufficient match between the two vectors, step three is done, which involves fitting the termini of the candidate (using, for example, a least squares procedure) to the termini of the gap. If these two termini fit well enough, the candidate is enrolled for a ranking process.

3 Claims, 19 Drawing Sheets

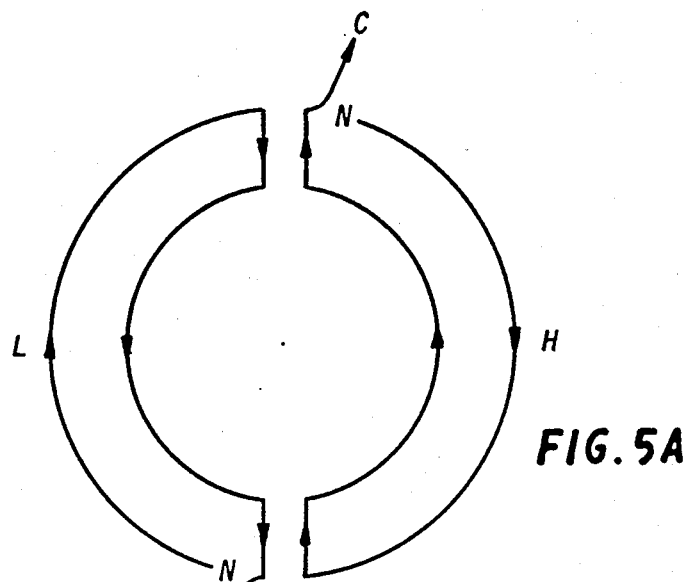
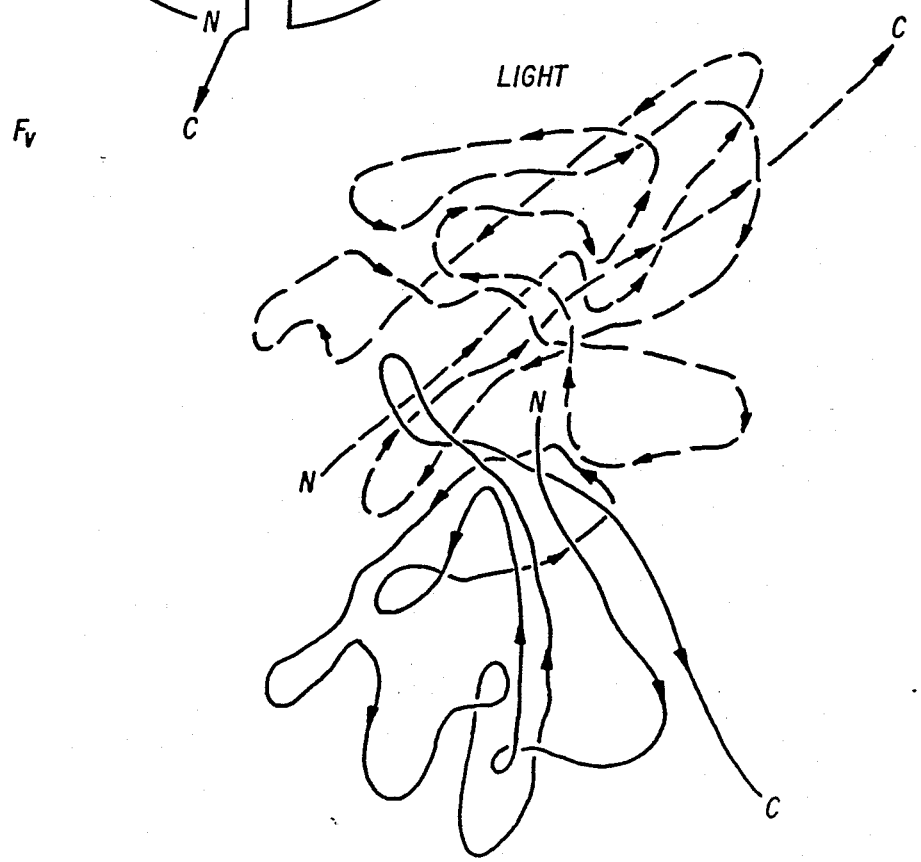
FIG. 5A
FIG. 5B

- REJECT CANDIDATE IF ANY ATOM OF LINKER COMES CLOSER THAN MINIMUM ALLOWED SEPARATION TO ANY RETAINED ATOM OF NATIVE STRUCTURE —1402
- PENALIZE CANDIDATE WHEN HYDROPHOBIC RESIDUES HAVE HIGH EXPOSURE TO SOLVENT —1404
- PENALIZE CANDIDATE WHEN HYDROPHYLIC RESIDUES HAVE LOW EXPOSURE TO SOLVENT —1406
- PROMOTE CANDIDATE WHEN HYDROPHOBIC RESIDUES HAVE LOW EXPOSURE TO SOLVENT —1408
- PROMOTE CANDIDATE WHEN HYDROPHYLIC RESIDUES HAVE HIGH EXPOSURE TO SOLVENT —1410
- PENALIZE CANDIDATE WHEN MAIN CHAIN FAILS TO FORM HYDROGEN BOND —1412
- PENALIZE CANDIDATE WHEN MAIN CHAIN MAKES USELESS EXCURSIONS INTO THE SOLVENT REGION —1414
- PROMOTE CANDIDATE WHEN MAIN CHAIN FORMS A HELIX —1416
- PROMOTE CANDIDATE WHEN MAIN CHAIN FORMS A BETA SHEET WHICH FITS AGAINST EXISTING BETA SHEETS —1418

FIG. 14

COMPUTER BASED SYSTEM AND METHOD FOR DETERMINING AND DISPLAYING POSSIBLE CHEMICAL STRUCTURES FOR CONVERTING DOUBLE- OR MULTIPLE-CHAIN POLYPEPTIDES TO SINGLE-CHAIN POLYPEPTIDES

This application is a continuation, of application Ser. No. 115,919, filed 11/2/87 abandoned, which is a continuation of Ser. No. 902,970 filed 9/2/86, now U.S. Pat. No. 4,704,692.

CROSS-REFERENCE TO RELATED APPLICATION

This application is related to application Ser. No. 902,971, also filed on Sept. 2, 1986 now abandoned.

BACKGROUND OF THE INVENTION

1. Field of the Invention The present invention relates to a computer assisted system and method for determining and displaying chemical structures useful in the design of single chain proteins.

2. Description of the Background Art

The advent of modern molecular biology and immunology has brought about the possibility of producing large quantities of biologically active materials in highly reproduceable form and with low cost. Briefly, the gene sequence coding for a desired natural protein is isolated, replicated (cloned) and introduced into a foreign host such as a bacterium, a yeast (or other fungi) or a mammalian cell line in culture, with appropriate regulatory control signals. When the signals are activated, the gene is transcribed and translated, and expresses the desired protein. In this hormones, enzymes or antibodies have been cloned and expressed in foreign hosts.

One of the problems with this approach is that it is limited by the "one gene, one polypeptide chain" principle of molecular biology. In other words, a genetic sequence codes for a single polypeptide chain. Many biologically active polypeptides, however, are aggregates of two or more chains. For example, antibodies are three-dimensional aggregates of two heavy and two light chains. In the same manner, large enzymes such as aspartate transcarbamylase, for example, are aggregates of six catalytic and six regulatory chains, these chains being different. In order to produce such complex materials by recombinant DNA technology in foreign hosts, it becomes necessary to clone and express a gene coding for each one of the different kinds of polypeptide chains. These genes can be expressed in separate hosts. The resulting polypeptide chains from each host would then have to be reaggregated and allowed to refold together in solution. Alternatively, the two or more genes coding for the two or more polypeptide chains of the aggregate could be expressed in the same host simultaneously, so that refolding and reassociation into the native structure with biological activity will occur after expression. The approach, however, necessitates expression of multiple genes, and as indicated, in some cases, in multiple and different hosts. These approaches have proved to be inefficient.

Even if the two or more genes are expressed in the same organism it is quite difficult to get them all expressed in the required amounts.

A classical example of multigene expression to form multimeric polypeptides is the expression by recombinant DNA technology of antibodies. Genes for heavy and light chains have been introduced into appropriate hosts and expressed, followed by reaggregation of these individual chains into functional antibody molecules (see for example Munro, *Nature*, 312:597 (1984); Morrison, S. L. *Science* 229:1202 (1985); Oi et al., *BioTechniques* 4:214 (1986).

Antibody molecules have two generally recognized regions in each of the heavy and light chains. These regions are the so-called "variable" region which is responsible for binding to the specific antigen in question, and the so-called "constant" region which is responsible for biological effector responses such as complement binding, etc. The constant regions are not necessary for antigen binding. The constant regions have been separated from the antibody molecule, and biologically active (i.e. binding) variable regions have been obtained.

The variable regions of an antibody are composed of a light chain and a heavy chain. Light and heavy chain variable regions have been cloned and expressed in foreign hosts, and maintain their binding ability (Moore et al, European Patent Publication 0088994 (published Sept. 21, 1983)).

It would be much more efficient if one could produce single polypeptide-chain molecules which have the same biological activity as the multiple chain aggregates such as, for example, multiple chain antibody aggregates or enzyme aggregates. Given the "one gene-one-polypeptide chain" principle, such single chain molecules would be more readily produceable, and would not necessitate multiple hosts or multiple genes in the cloning and expression. In order to accomplish this, it is first necessary to devise a method for generating single chain structures from two-chain aggregate structures, wherein the single chain will retain the three-dimensional folding of the separate natural aggregate of two polypeptide chains.

While the art has discussed the study of proteins in three dimensions, and has suggested modifying their architecture (see, for example, the article "Protein Architecture: Designing from the Ground Up," by Van Brunt, J., *BioTechnology*, 4: 277–283 (April, 1986, the problem of generating single chain structures from multiple chain structures, wherein the single chain structure will retain the three-dimensional architecture of the multiple chain aggregate, has not been satisfactorily addressed.

SUMMARY OF THE INVENTION

The present invention provides a computer based method for generating single chain polypeptides from two polypeptide chain aggregates and then analyzing and displaying the results using computer graphics.

A computer based system and method is used to determine and display possible chemical structures for converting two naturally aggregated but chemically separated polypeptide chains into a single polypeptide chain which will fold into a three dimensional structure very similar to the original structure made of the two polypeptide chains.

A data base is used which contains a large number of amino acid sequences for which the three dimensional structure is known. After plausible sites have been selected, this data base is examined to find which amino acid sequences (linkers) can bridge the gap between the plausible sites without significant local strain to create a plausible one-polypeptide structure which retains most of the three dimensional features of the original aggregate molecule.

The testing of each possible linker proceeds in three steps. First, the span (a scalar quantity) of the candidate is compared to the span of the gap. If the span is close enough, step two is done which involves aligning the first peptide of the candidate with the initial peptide of the gap. The three dimensional vector from tail to head of the candidate is compared to the three dimensional vector from tail to head of the gap. If there is a sufficiently good match between the two vectors, step three is done, which involves fitting the termini of the candidate (using, for example, a least squares procedure) to the terminii of the gap. If these two termini fit well enough, the candidate is enrolled for a ranking process. The candidates are ranked from most plausible to least plausible by an expert operator using an interactive computer graphics approach of observing the interactions between the linker with all retained portions of the native polypeptide aggregate. The most plausible candidate typically is the fragment that can bridge the two plausible sites to form a single polypeptide chain, where the bridge will least distort the resulting three dimensional folding of the single polypeptide chain from the natural folding of the aggregate of the two originally separate chains.

In one specific embodiment, the invention provides:

A computer based method for determining possible amino acid or peptide chemical structures for converting a two chain polypeptide to a single chain polypeptide fragment, comprising the steps of:

(1) creating a first group of possible candidates having a correct length for bridging a first plausible site on the first chain of the multiple chain polypeptide to a second plausible site on the second chain of said polypeptide by examining a data base of possible candidates;

(2) producing a second group of possible candidates by determining those candidates in the first group having a proper direction for bridging the two plausible sites;

(3) producing a third group of possible candidates by determining which of the candidates in the second group have a proper orientation for bridging the two plausible sites; and (4) displaying the candidates in the third group to the user using computer graphics, whereby the user can view the possible candidates in three dimensions.

BRIEF DESCRIPTION OF THE DRAWINGS

The present invention as defined in the claims can be better understood with reference to the text and to the following drawings, as follows:

FIG. 5A is a schematic two dimensional simplified representation of the light chain L and heavy chain H of two naturally aggregated antibody variable region $F_v$ polypeptide chains used to illustrate the site selection process.

FIG. 5B is a two dimensional representation of the three dimensional relationship of the two aggregated polypeptide chains showing the light chain L (----) and the heavy chain H (-) of the variable region of one antibody.

by linker 1 (----) to produce a single chain antibody.

Figure 8A:
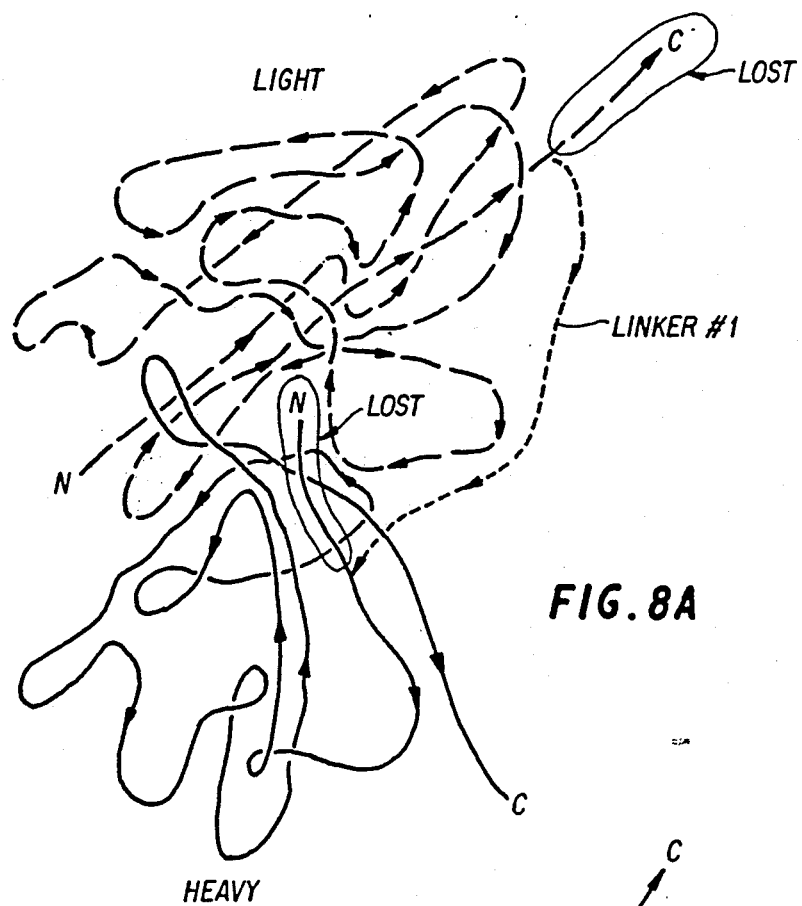
FIG. 8A is a two dimensional simplified schematic diagram of a single chain antibody linking together two separate chains ((Heavy) and (light))
Figure 8B:
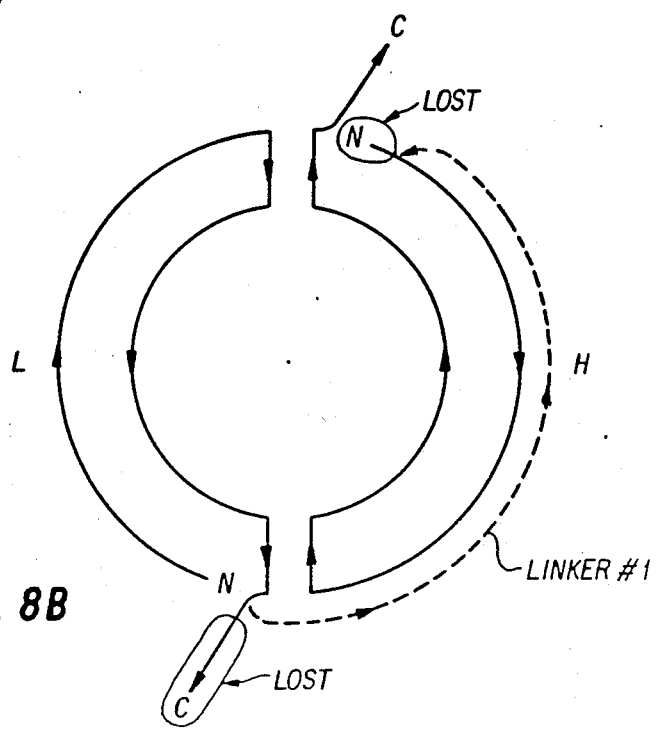

FIG. 8B is a two dimensional representation showing a single chain antibody produced by linking two aggregated polypeptide chains using linker 1.

Figure 9:
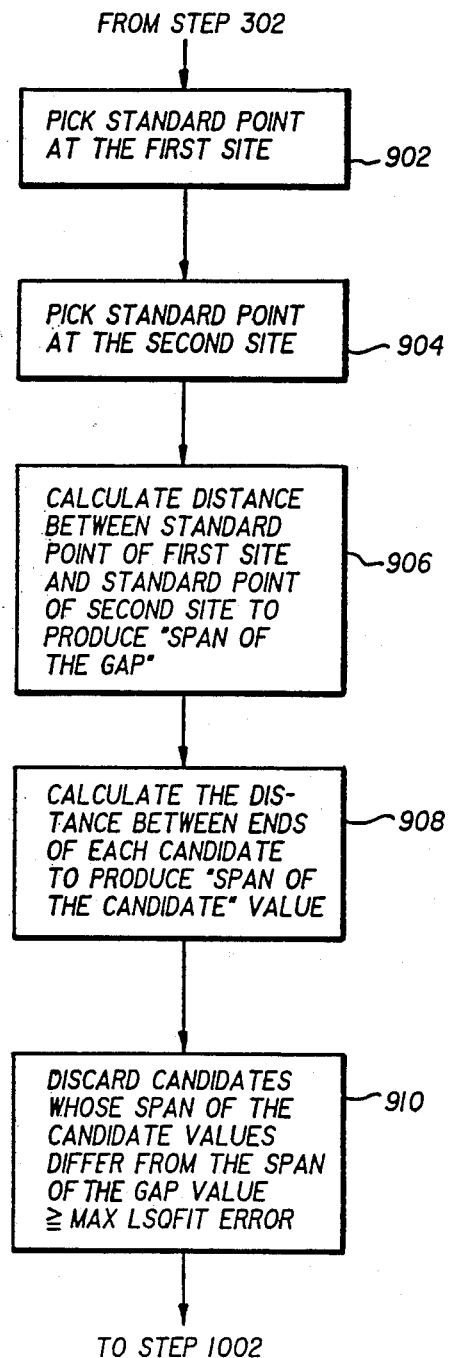

FIG. 9 shows a block diagram of candidate selection for correct span.

Figure 10:
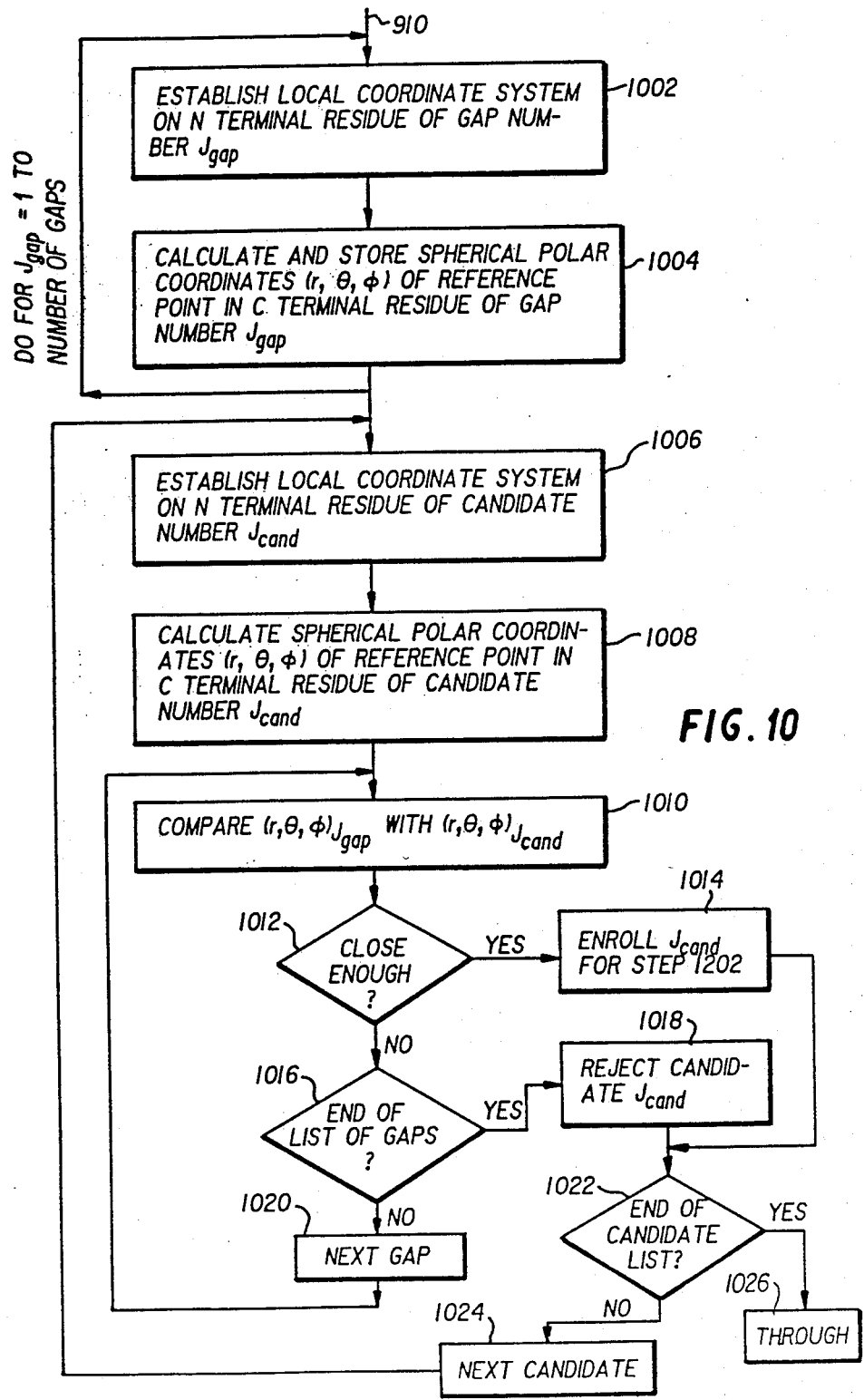

FIG. 10 shows a block diagram of candidate selection for correct direction from N terminal to C terminal.

Figure 11A:
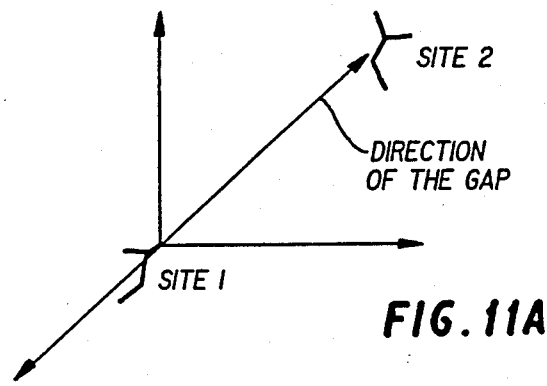
Figure 11B:
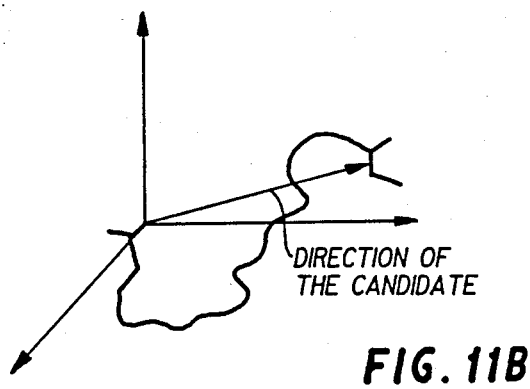
Figure 11C:
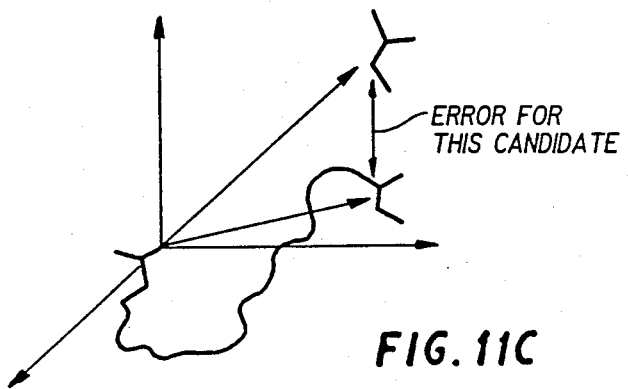

FIGS. 11A-11C show a comparison of direction of a gap to direction a candidate.

Figure 12:
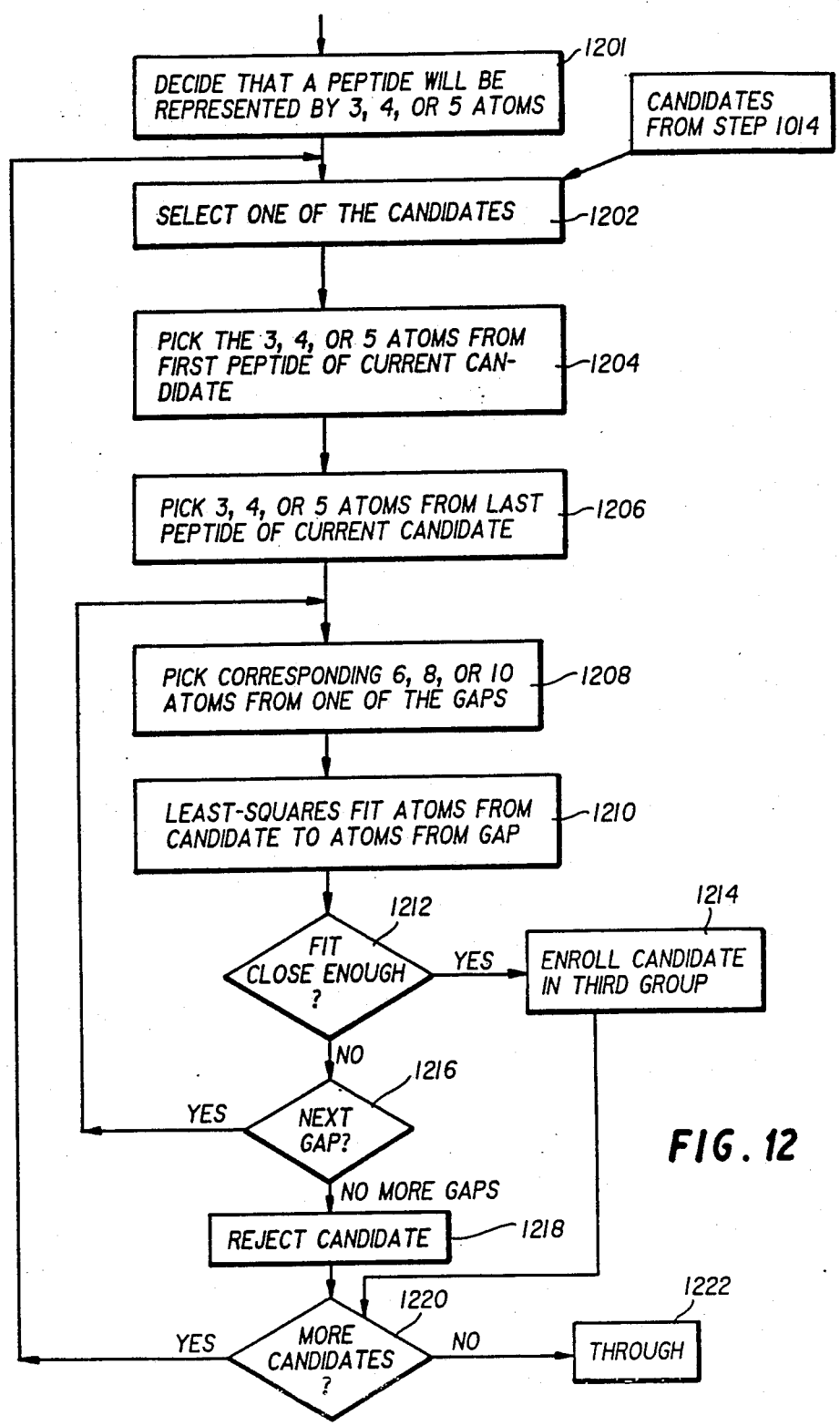

FIG. 12 shows a block diagram of candidate selection for correct orientation at both ends.

Figure 13:
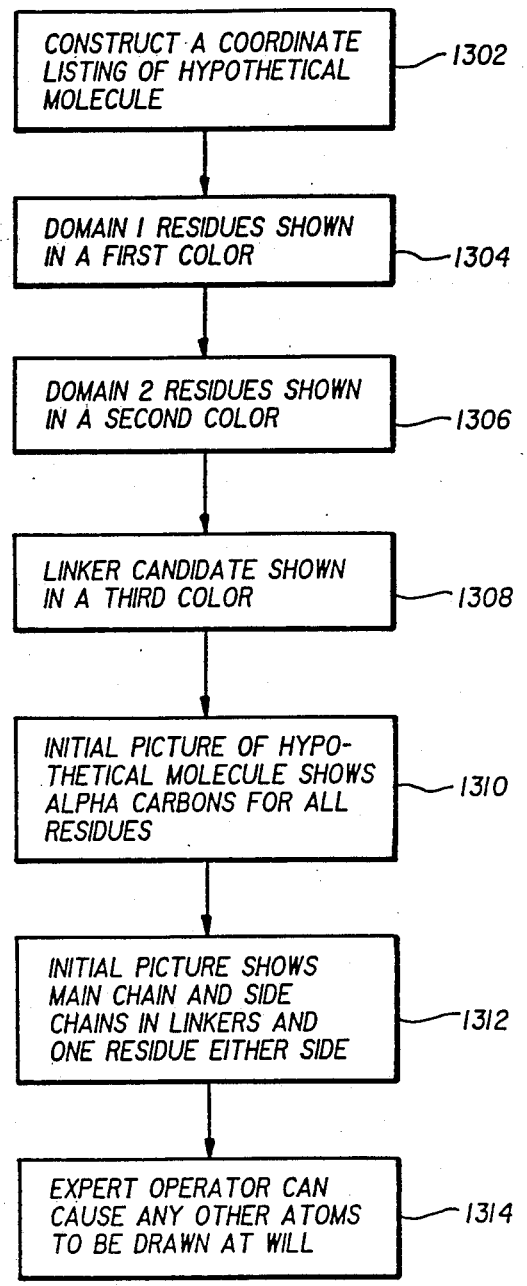

FIG. 13 shows a block diagram of selection of sites for the two-linker embodiment.

FIG. 14 shows examples of rules by which candidates may be ranked.

Figure 15A:
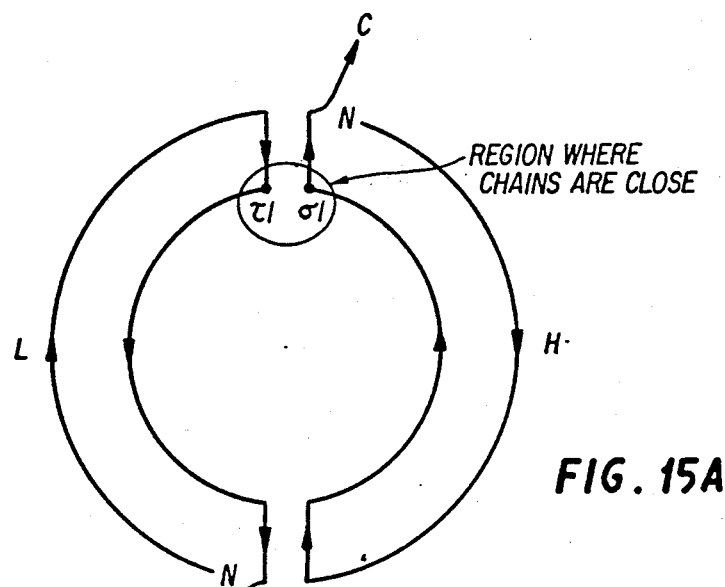

FIG. 15A shows a two-dimensional simplified representation of the variable domain of an Fv light chain, L, and the variable domain of an Fv heavy chain, H, showing the first two sites to be linked.

Figure 15B:
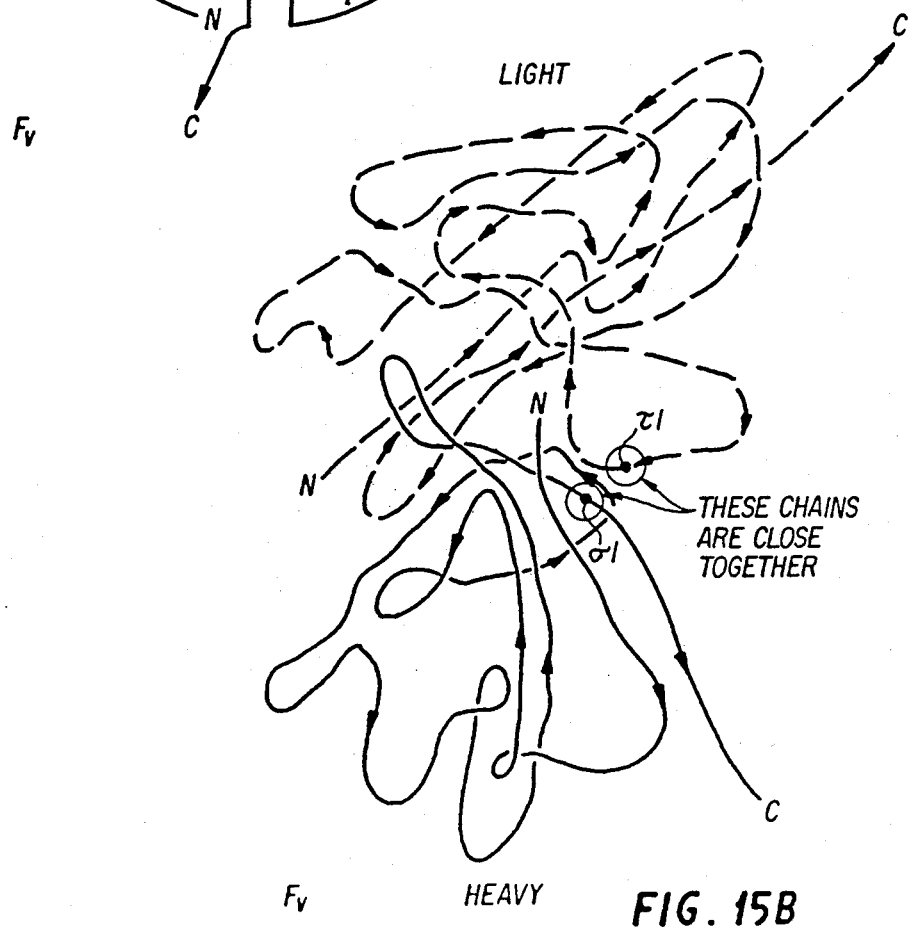

FIG. 15B shows a two-dimensional representatin of the three-dimensional relationships between the variable domain of an Fv light chain, L, and the variable domain of an Fv heavy chain, H, showing the regions in which the second sites to be linked can be found and the linker between the first pair of sites.

Figure 16A:
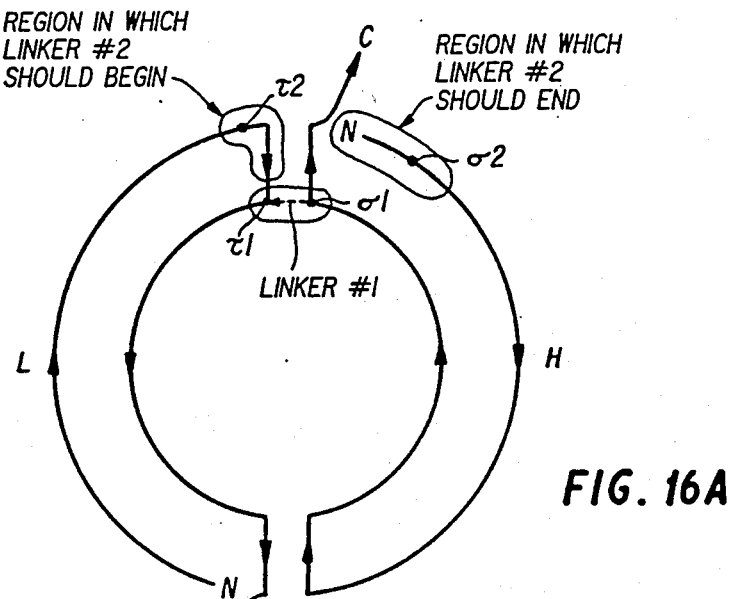

FIG. 16A shows the two-dimensional simplified representation of the variable domain of an Fv light chain, L, and the variable domain of an Fv heavy chain, H, showing the regions in which the second sites to be linked can be found and the linker between the first pair of sites.

Figure 16B:
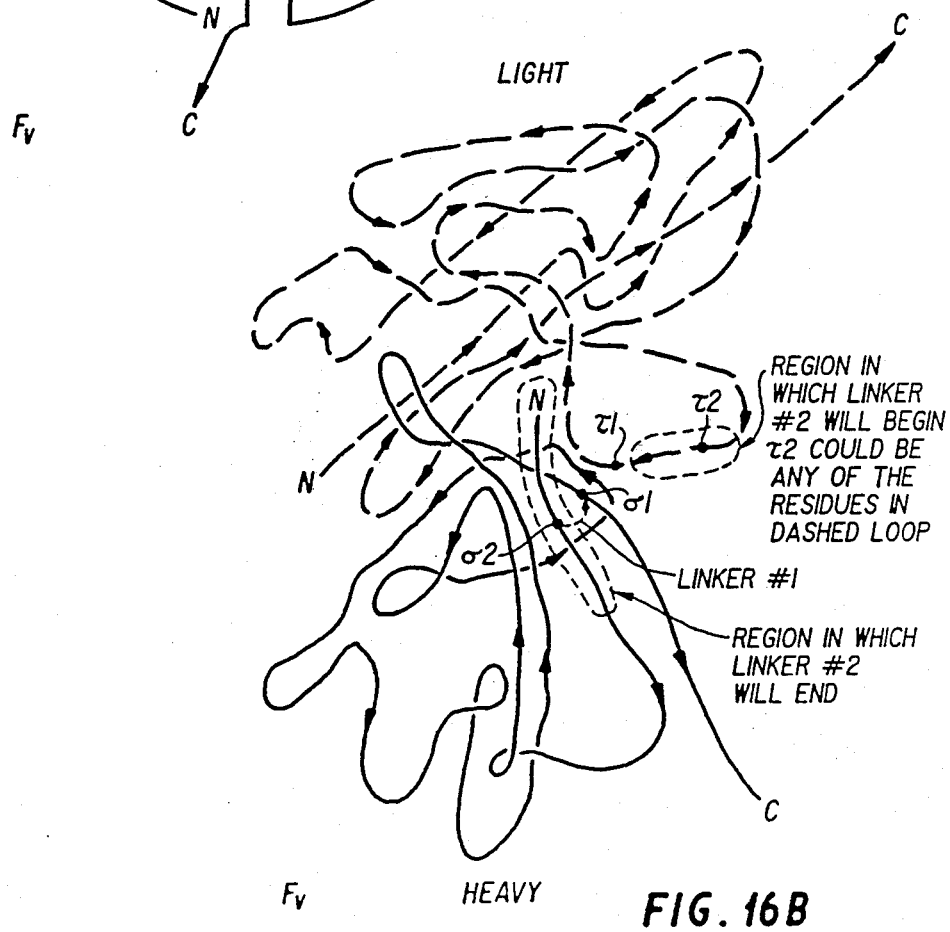

FIG. 16B shows the two-dimensional representation of the three-dimensional relationships between the variable domain of an Fv light chain, L, and the variable domain of an Fv heavy chain, H, showing the regions in which the second sites to be linked can be found and the linker between the first pair of sites.

Figure 17A:
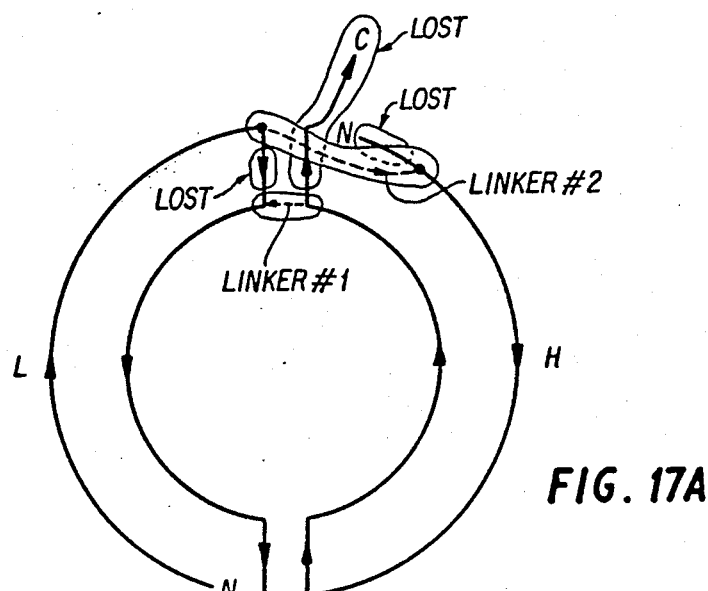

FIG. 17A shows the two-dimensional simplified representation of the variable domain of an Fv light chain, L, and the variable domain of an Fv heavy chain, H, showing the second linker and the portions of the native protein which are lost.

Figure 17B:
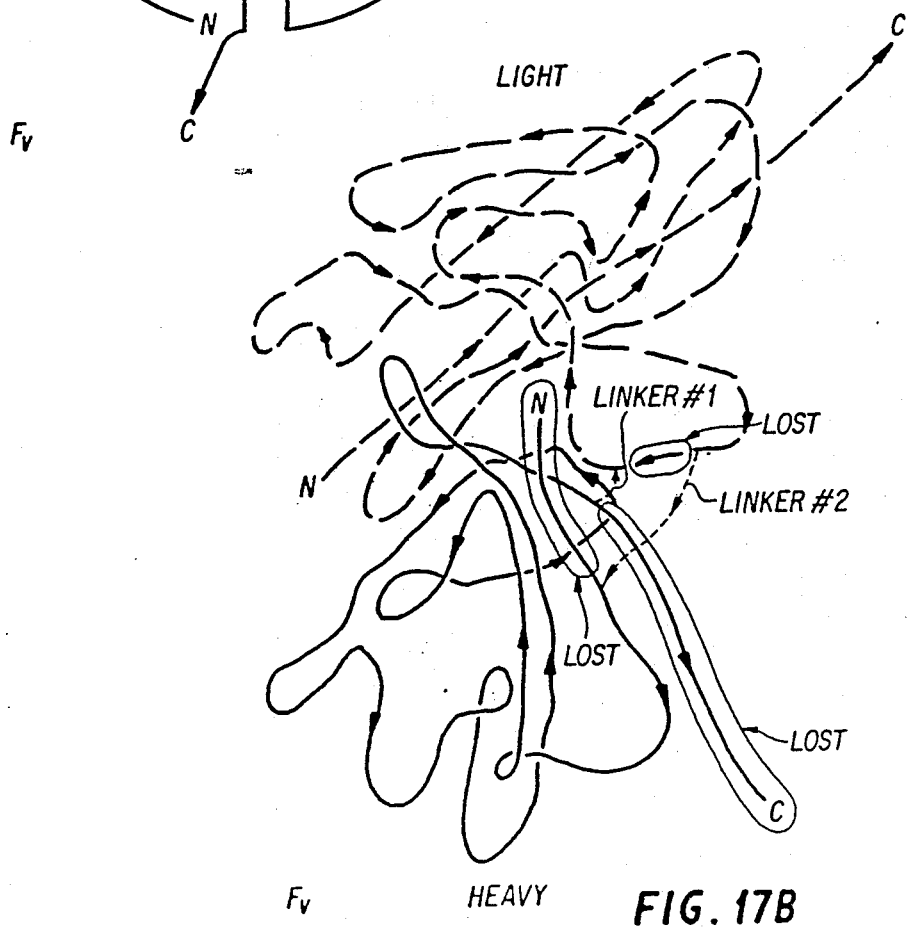

FIG. 17B shows the two-dimensional representation of the three-dimensional relationships between the variable domain of an Fv light chain, L, and the variable domain of an Fv heavy chain, H, showing the second linker and the portions of native protein which are lost.

Figure 18:
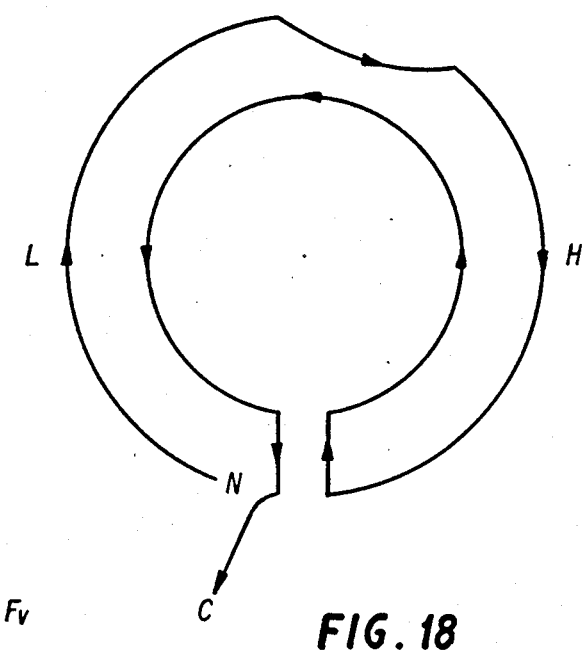

FIG. 18 shows the two-dimensional simplified representation of the variable domain of an Fv light chain, L, and the variable domain of an Fv heavy chain, H, showing the complete construction.

Figure 19:
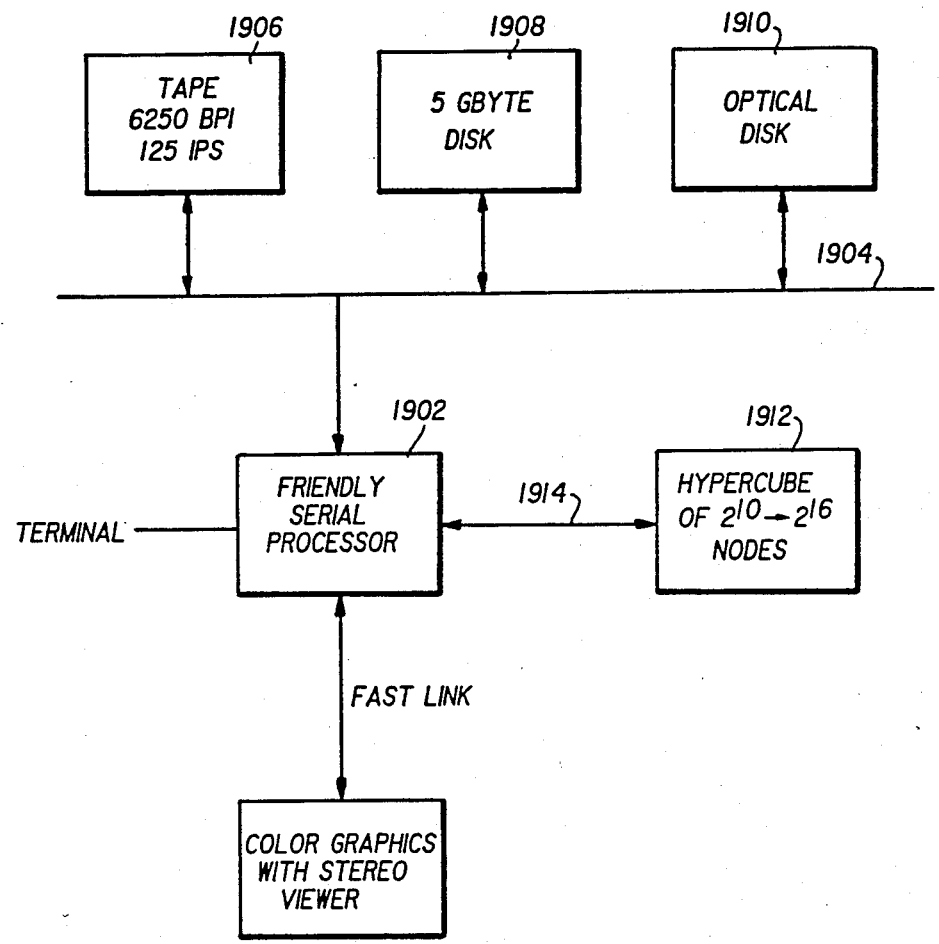

FIG. 19 shows a block diagram of the parallel processing mode of the present invention.

Figure 20A:
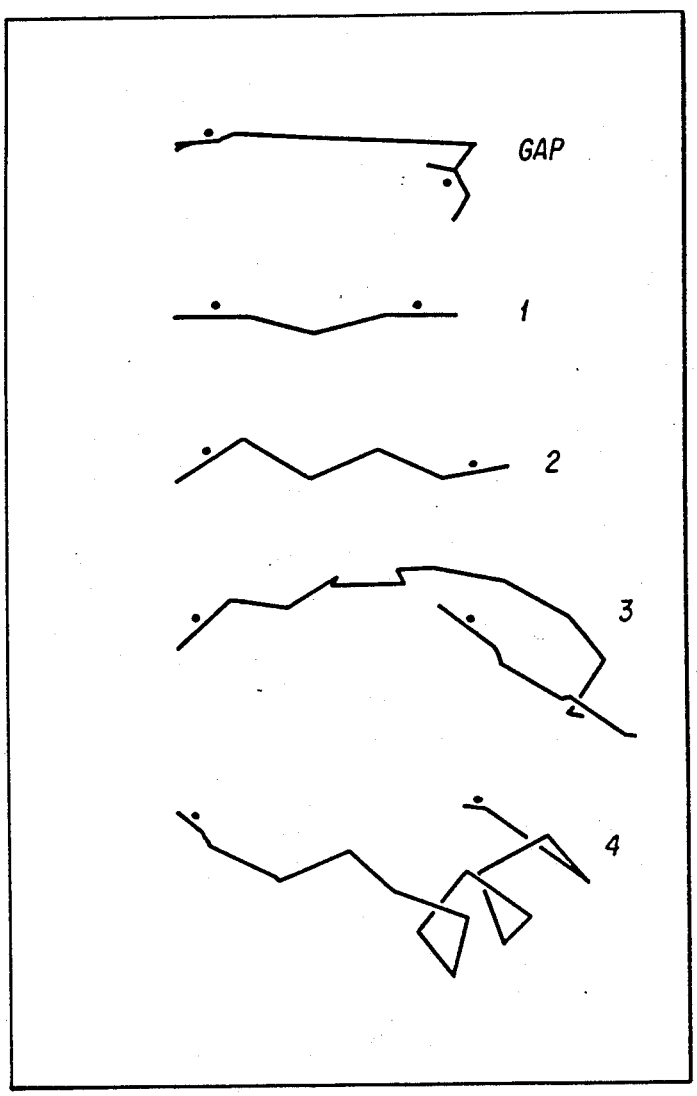

FIG. 20A shows five pieces of molecular structure. The uppermost segment consists of two peptides joined by a long line. The separation between the peptides is 12.7A. The first C alpha of each peptide lies on the X-axis. The two dots indicate the standard reference point in each peptide.

Below the gap are four linker candidates (labeled 1,2,3 & 4), represented by a line joining the alpha carbons. In all cases, the first and penultimate alpha carbons are on lines parallel to the X-axis, spaced 8.0 apart. Note that the space between dots in linker 1 is much shorter than in the gap.

Figure 20B:
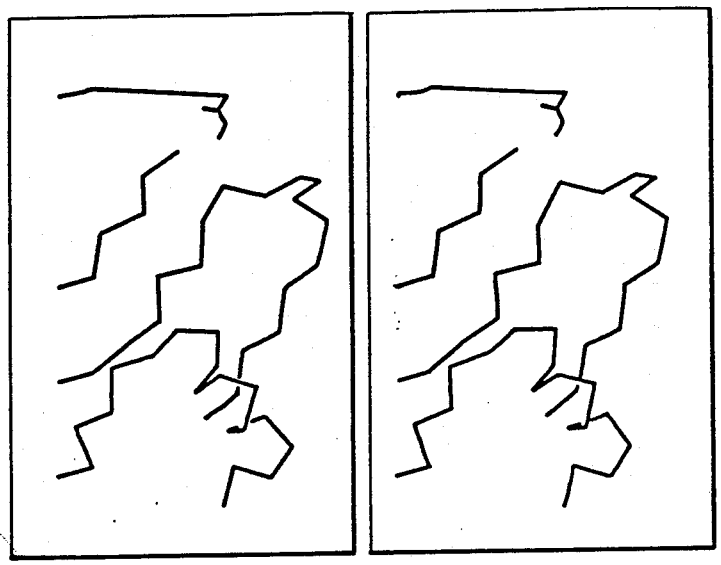

FIG. 20B shows the initial peptides of linkers 2, 3, and 4 which have been aligned with the first peptide of the gap. For clarity, the linkers have been translated vertically to their original positions.

The vector from the first peptide in the gap to the second peptide in the gap lies along the X-axis, a corresponding vector for linkers 3 nnd 4 also lies along the X-axis. Linker 2, however, has this vector pointing up and to the right, thus linker 2 is rejected.

Figure 20C:
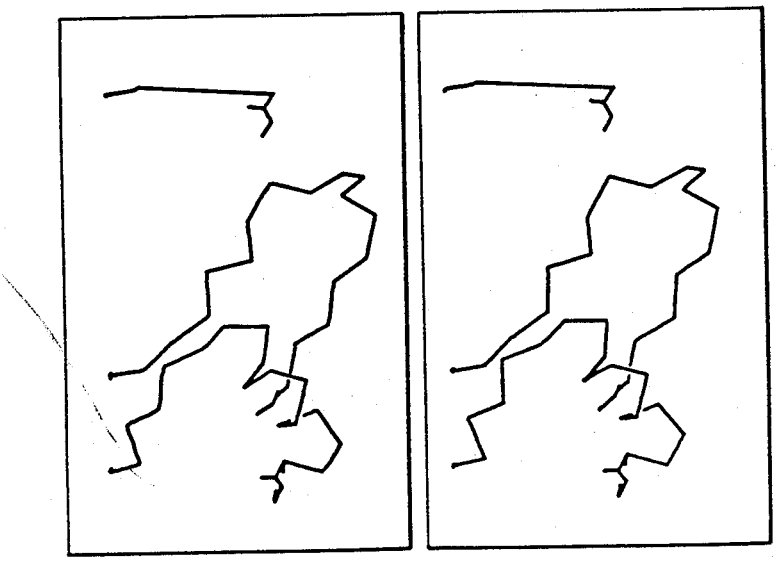

FIG. 20C shows the ten atms which compose the initial and final peptides of linkers 3 and 4, which have been least-squares fit to the corresponding atoms from the gap. These peptides have been drawn in. Note that in the gap and in linker 4 the final peptide points down and lies more-or-less in the plane of the paper. In linker 3, however, this final peptide points down and to the left and is twisted about 90 degrees so that the carbonyl oxygen points toward the viewer. Thus linker 3 is rejected. Sections B and C are stereo diagrams which may be viewed with the standard stereo viewer provided.

DETAILED DESCRIPTION OF THE PREFERRED EMBODIMENTS

Table of Contents

I. General Overview
II. Hardware and Software Environment
III. Single Linker Embodiment
  A. Plausible Site Selection
  B. Selection of Candidates
    1. Selecting Candidates with Proper Distance Between the N Terminal and the C Terminal.
    2. Selecting Candidates With Proper Direction from the N Terminal to the C Terminal.
    3. Selecting Candidates With Proper Orientation between the termini.
  C. Ranking and Eliminating Candidates
C IV. Double and Multiple Linker Embodiments
  A. Plausible Site Selection
  B. Candidate Selection and Candidate Rejection Steps
Parallel Processing Embodiment

I. General Overview

The present invention is a computer based system and method for determining and displaying possible chemical structures (linkers) for converting two naturally aggregated but chemically separate polypeptide chains into a single polypeptide chain which will fold into a three dimensional structure very similar to the original structure made of two polypeptide chains. The original structure is referred to hereafter as "native protein."

The first general step of the three general steps of the present invention involves selection of plausible sites to be linked. In the case of a single linker, criteria are utilized to select a plausible site on each of the two polypeptide chains which will result in (1) a minimum loss of residues from the native polypeptide chains and (2) a linker of minimum number of amino acids consistent with the need for stability. A pair of sites defines a gap to be bridged or linked. A two-or-more-linker approach is adopted when a single linker cannot achieve the two stated goals. In both the single-linker case and the two-or-more-linker case, more than one gap may be selected for use in the second general step.

The second general step of the present invention involves examining a data base to determine possible linkers to fill the plausible gaps selected in the first general step, so that candidates can be enrolled for the third general step. Specifically, a data base contains a large number of amino acid sequences for which the three-dimensional structure is known. In the second general step, this data base is examined to find which amino acid sequences can bridge the gap or gaps to create a plausible one-polypeptide structure which retains most of the three dimensional features of the native (i.e. original aggregate) molecule. The testing of each possible linker proceeds in three general substeps. The first general substep utilizes the length of the possible candidate. Specifically, the span or length (a scaler quantity) of the candidate is compared to the span of each of the gaps. If the difference between the length of the candidate and the span of any one of the gaps is less than a selected quantity, then the present invention proceeds to the second general substep with respect to this candidate. FIG. 20A shows one gap and four possible linkers. The first linker fails the first general substep because its span is quite different from the span of the gap.

In the second general substep, called the direction substep, the initial peptide of the candidate is aligned with the initial peptide of each gap. Specifically, a selected number of atoms in the initial peptide of the candidate are rotated and translated as a rigid body to best fit the corresponding atoms in the initial peptide of each gap. The three dimensional vector (called the direction of the linker) from the initial peptide of the candidate linker to the final peptide of the candidate linker is compared to the three dimensional vector (call the direction of the gap) from the initial peptide of each gap to the final peptide of the same gap. If the ends of these two vectors come within a preselected distance of each other, the present invention proceeds to the third general substep of the second general step with respect to this candidate linker.

FIG. 20B shows one gap and three linkers. All the linkers have the correct span and the initial peptides have been aligned. The second linker fails the second general substep because its direction is quite different from that of the gap; the other two linkers are carried forward to the third general substep of the second general step.

In the third general substep of the second step of the present invention, the orientations of the terminal peptides of each linker are compared to the orientations of the terminal peptides of each gap. Specifically, a selected number of atoms (3, 4, or 5; 5 in the preferred embodiment) from the initial peptide of the candidate plus the same selected number of atoms (3, 4, or 5; 5 in the preferred embodiment) from final peptide of the candidate are taken as a rigid body. The corresponding atoms from one of the gaps (viz 5 from the initial peptide and 5 from the final peptide) are taken as a second rigid body. These two rigid bodies are superimposed by a least-squares fit. If the error for this fit is below some preselected value, then the candidate passes the third general substep of the second general step and is enrolled for the third general step of the present invention. If the error is greater than or equal to the preselected value, the next gap is tested. When all gaps have been tested without finding a sufficiently good fit, the candidate is abandoned.

The third general step of the present invention results in the ranking of the linker candidates from most plausible to least plausible. The most plausible candidate is the fragment that can bridge the two plausible sites of one of the gaps to form a single polypeptide chain, where the bridge will least distort the resulting three dimensional folding of the single polypeptide chain from the natural folding of the aggregate of the two originally chemically separate chains.

In this third general step of the present invention, an expert operator uses an interactive computer-graphics approach to rank the linker candidates from most plausible to least plausible. This ranking is done by observing the interactions between the linker candidate with all retained portions of the native protein. A set of rules are used for the ranking. These expert system rules can be built into the system so that the linkers are displayed only after they have satisfied the expert system rules that are utilized.

The elected candidate offers to the user a linked chain structure having a very significantly increased probability of proper folding than would be obtained using a random selection process. This means that the genetic engineering aspect of creating the desired single polypeptide chain is significantly reduced since the number of candidates that have to be genetically engineered in practice is reduced by a corresponding amount. The most plausible candidates can be used to genetically engineer actual molecules.

The parameters of the various candidates can be stored for later use. They can also be provided to the user either visually or recorded on a suitable media (paper, magnetic tape, color slides, etc.). The results of the various steps utilized in the design process can also be stored for later use or examination.

The present invention can be programmed so that certain expert rules are utilized as a first general substep in the third general step to rank candidates and even eliminate unsuitable candidates before visual inspection by an expert operator, which would be the second general substep of the third general step. These expert rules assist the expert operator in ranking the candidates from most plausible to least plausexperimental data on linkers produced by the system and methods of the present invention.

The most plausible candidate is a genetically producible single polypeptide chain which has a very significantly higher probability (a million or more as compared to a random selection) of folding into a three dimensional structure very similar to the original structure made of the two polypeptide chains than would be produced if random selection of the linker was done. In this way, the computer based system and method of the present invention can be utilized to engineer single polypeptide chains by using one or more linkers which convert naturally aggregated but chemically separated polypeptide chains into the desired single chain.

The present invention operates on a conventional minicomputer system having storage devices capable of storing the amino acid sequence-structure data base, the various application programs utilized by the present invention, and the parameters of the possible linker candidates that are being evaluated.

The minicomputer CPU is connected by a suitable serial processor structure to an interactive computer-graphics display system. Typically, the interactive computer-graphics display system comprises a display terminal with resident three-dimensional application software and associated input and output devices, such as X/Y plotters, position control devices (potentiometers, an x-y tablet, or a mouse), and keyboard.

The interactive computer-graphics display system allows the expert operator to view the chemical structures being evaluated in the design process of the present invention. Graphics and programs are used to select the gaps (Gen. Step 1) and to rank candidates (Gen. Step 3). Essentially, it operates in the same fashion for the single-linker embodiment and for the two-or-more-linker embodiments.

For example, during the first general step of the present invention, the computer-graphics interactive display system allows the expert operator to visually display in three dimensions the two naturally aggregated but chemically separate polypeptide chains. Using three dimensional software resident in the computer-graphics display system, the visual representation of the two separate polypeptide chains can be manipulated as desired. For example, the portion of the chain(s) being viewed can be magnified electronically, and such magnification can be performed in a zoom mode. Conversely, the image can be reduced in size, and this reduction can also be done in a reverse zoom mode. The position of the portion of the molecule can be translated, and the displayed molecule can be rotated about any one of the three axes (x, y and z). Specific atoms in the chain can be selected with an electronic pointer. Selected atoms can be labeled with appropriate text. Specific portions of native protein or linker can be identified with color or text or brightness. Unwanted portions of the chain can be erased from the image being displayed so as to provide the expert operator with a visual image that represents only a selected aspect of the chain(s). Atoms selected by pointing or by name can be placed at the center of the three dimensional display; subsequent rotation uses the selected atom as the origin. These and other display aspects provide the expert operator with the ability to visually represent portions of the chains which increase the ability to perform the structural design process.

One of the modes of the present invention utilizes a serial computational architecture. This architecture using present equipment requires approximately four to six hours of machine and operator time in order to go through the various operations required for general steps for a particular selection of gaps. Obviously, it would be desirable to significantly reduce the time since a considerable portion thereof is the time it takes for the computer system to perform the necessary computational steps.

An alternate embodiment of the present invention utilizes a parallel processing architecture. This parallel processing architecture significantly reduces the time acquired to perform the necessary computational steps. A hypercube of a large number of nodes can be utilized so that the various linkers that are possible for the selected sites can be rapidly presented to the expert system operator for evaluation.

Since there are presently between 200 and 300 known protein three-dimensional structures, the parallel processing approach can be utilized. There currently are computers commercially available that have as many as 1,024 computing nodes.

Using a parallel processing approach, the data base of observed peptide structures can be divided into as many parts as there are computing nodes. For example, if there are structures for 195 proteins with 219 amino acids each, one would have structures for $195 \times 218$ dipeptides, $195 \times 217$ tripeptides, $195 \times 216$ tetrapeptides, etc. One can extract all peptides up to some length n. For example, if n were 30, one would have $195 \times 30 \times 204$ peptides. Of course, proteins vary in length, but with 100 to 400 proteins of average length 200 (for example), and for peptide linkers up to length 30 amino acids (or any other reasonable number), one will have between 1,000,000 and 4,000,000 peptide structures. Once the peptides have been extracted and labeled with the protein from which they came, one is free to divide all the peptides as evenly as possible among the available computing nodes.

The parallel processing mode operates as follows. The data base of known peptides is divided among the available nodes. Each gap is sent to all the nodes. Each node takes the gap and tests it against those peptides which have been assigned to it and returns information about any peptides which fit the gap and therefore are candidate linkers. As the testing for matches between peptides and gaps proceeds independently in each node, the searching will go faster by a factor equal to the number of nodes.

A first embodiment of the present invention utilizes a single linker to convert two naturally aggregated but chemically separate polypeptide chains into a single polypeptide chain which will fold into a three dimensional structure very similar to the original structure made of two polypeptide chains.

A second embodiment utilizes two or more linkers to convert the two polypeptide chains into the desired single polypeptide chain. The steps involved in each of these embodiments utilizing the present invention are illustrated in the explanations below.

The process of designing a single polypeptide chain from two initially separate chains can also be applied to multi chain aggregates of polypeptide chains. For example, given an aggregate of n chains, any neighboring pair can be linked by the methods of the invention to produce a new aggregate of n−1 chains. Any neighboring pair of this new aggregate can then be linked to produce a new aggregate of n−2 chains, and so on. The iteration can be repeated as many times as desired. Ultimately, a single polypeptide chain can be produced from any aggregate.

Alternatively, the process of designing a single polypeptide chain from a multi chain aggregate thereof can be done in parallel instead of serially. The linker design method of the invention can be applied simultaneously to the n chains, to produce a single chain. The parallel processing embodiment (see below Section V) discusses possible ways of carrying out the parallel design embodiment.

II. Hardware and Software Environment

Figure 1:
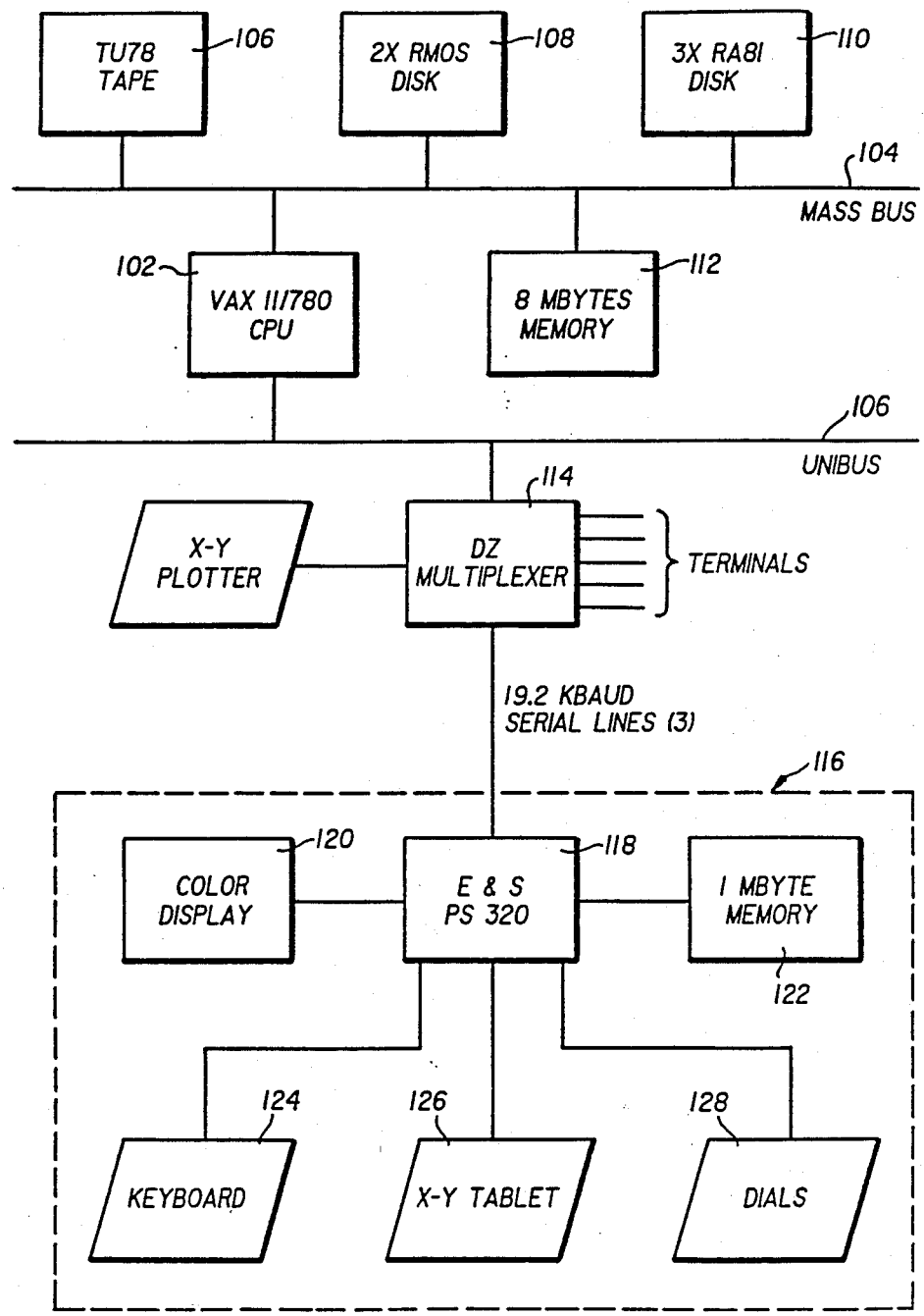
FIG. 1 is a block diagram of the hardware aspects of the serial processor mode of the present invention.

A block diagram of the hardware aspects of the present invention is found in FIG. 1. A central processing unit (CPU) 102 is connected to a first bus (designated massbus 104) and to a second bus (designated Unibus 106). A suitable form for CPU 102 is a model Vax 11/780 made by Digital Equipment Corporation of Maynard, Mass. Any suitable type of CPU, however, can be used.

Bus 104 connects CPU 102 to a plurality of storage devices. In the best mode, these storage devices include a tape drive unit 106. The tape drive unit 106 can be used, for example, to load into the system the data base of the amino acid sequences whose three dimensional structures are known. A suitable form for tape drive 106 is a Digital Equipment Corporation model TU 78 drive, which operates at 125 inches per second, and has a 1600–6250 bit per inch (BPI) dual capability. Any suitable type of tape drive can be used, however.

Another storage device is a pair of hard disk units labeled generally by reference numeral 108. A suitable form for disk drive 108 comprises two Digital Equipment Corporation Rmo5 disk drives having, for example, 256 Mbytes of storage per disk. Another disk drive system is also provided in the serial processor mode and is labeled by reference numeral 110. This disk drive system is also connected to CPU 102 by bus 104. A suitable form for the disk system 110 comprises three Digital Equipment Corporation model Ra 81 hard disk drives having, for example, 450 Mbytes of storage per disk.

Dynamic random access memory is also provided by a memory stage 112 also connected to CPU 102 by bus 104. Any suitable type of dynamic memory storage device can be used. In the serial processor mode, the memory is made up of a plurality of semi-conductor storage devices found in a DEC model Ecc memory unit. Any suitable type of dynamic memory can be employed.

The disk drives 108 and 110 store several different blocks of information. For example, they store the data base containing the amino acid sequences and structures that are read in by the tape drive 106. They also store the application software package required to search the data base in accordance with the procedures of the present invention. They also store the documentation and executables of the software. The hypothetical molecules that are produced and structurally examined by the present invention are represented in the same format used to represent the protein structures in the data base. Using this format, these hypothetical molecules are also stored by the disk drives 108 and 110 for use during the structural design process and for subsequent use after the process has been completed.

A Digital Equipment Corporation VAX/VMS (DEC Trademark) operating system allows for multiple users and assures file system integrity. It provides virtual memory, which relieves the programer of having to worry about the amount of memory that is used. Initial software was developed under versions 3.0 to 3.2 of the VAX/VMS operating system. The serial processor mode currently is running on version 4.4. DEC editors and FORTRAN compiler were utilized.

The CPU 102 is connected by Bus 106 to a multiplexer 114. The multiplexer allows a plurality of devices to be connected to the CPU 102 via bus 106. A suitable form for multiplexer 114 is a Digital Equipment Corporation model Dz 16 terminal multiplexer. In the preferred embodiment, two of these multiplexers are used. The multiplexer 114 supports terminals (not shown in FIG. 1) and the serial communications (at 19.2 Kbaud, for example) to the computer-graphics display system indicated by the dash lined box 116.

The computer-graphics display system 116 includes a electronics stage 118. The electronic stage 118 is used for receiving the visual image prepaired by CPU 102 and for displaying it to the user on a display (typically one involving color) 120. The electronic stage 118 in connection with the associated subsystems of the computer-graphics display system 116 provide for local control of specific functions, as described below. A suitable form of the electronics system 118 is a model PS 320 made by Evans & Sutherland Corp. of Salt Lake, Utah. A suitable form for the display 120 is either a 25 inch color monitor or a 19 inch color monitor from Evans & Sutherland.

Dynamic random access memory 122 is connected to the electronic stage 118. Memory 122 allows the electronic system 118 to provide the local control of the image discussed below. In addition, a keyboard 124 of conventional design is connected to the electronic stage 118, as is an x/y tablet 126 and a plurality of dials 128. The keyboard 124, x/y tablet 126, and dials 128 in the serial processor mode are also obtained from Evans & Sutherland.

The computer generated graphics system 116, as discussed above, receives rom CPU 102 the image to be displayed. It provides local control over the displayed image so that specific desired user initiated functions can be performed, such as:

(1) zoom (so as to increase or decrease the size of the image being displayed);

(2) clipping (where the sides, front or back of the image being displayed are removed);

(3) intensity depth queueing-(where objects further away from the viewer are made dimmer so as to provide a desired depth effect in the image being displayed);

(4) translation of the image in any of the three axes of the coordinate system utilized to plot the molecules being displayed;

(5) rotation in any of the three directions of the image being displayed;

(6) on/off control of the logical segments of the picture. For example, a line connecting the alpha carbons of the native protein might be one logical segment; labels on some or all of the residues of the native protein might be a second logical segment; a trace of the alpha carbons of the linker(s) might be a third segment; and a stick figure connecting Carbon, Nitrogen, Oxygen, and Sulphur atoms of the linker(s) and adjacent residue of the native protein might be a fourth logical segment. The user seldom wants to see all of these at once; rather the operator first becomes oriented by viewing the first two segments at low magnification. Then the labels are switched off and the linker carbon trace is turned on. Once the general features of the linker are seen, the operator zooms to higher magnification and turns on the segments which hold more detail;

(7) selection of atoms in the most detailed logical segment. Despite the power of modern graphics, the operator can be overwhelmed by too much detail at once. Thus, the operator will pick one atom and ask to all amino acids within some radius of that atom, typ 6 Angstroms, but other radii can be used. The user may also specify that certain amino acids will be included in addition to those that fall within the specified radius of the selected atom;

(8) changing of the colors of a various portion of the image being displayed so as to indicate to the viewer particular information using visual queueing.

As stated above, the serial processor mode of the present invention currently is running the application software on version 4.4 of the Vax/Vms operating system used in conjunction with CPU 102. The application programs were programmed using the FLECS (FORTRAN Language with Extended Control Sections) programming language written in 1974 by Terry Beyer of the University of Oregon, Eugene, Oreg. The FLECS is a FORTRAN preprocessor, which allows more logical programming. All of the code used in the serial processor mode was developed in FLECS. It can be appreciated, however, that the present invention encompasses other operating systems and programming languages.

The macromolecules displayed on color display 120 of the computer-graphics display system 116 utilize an extensively modified version of version 5.6 of FRODO. FRODO is a program for displaying and manipulating macromolecules. FRODO was written by T. A. Jones at Max Planck Institute for Biochemistry, Munich, West Germany, for building or modeling in protein crystallography. FRODO version 5.6 was modified so as to be driven by command files; programs were then written to create the command files. It is utilized by the electronic stage 118 to display and manipulate images on the color display 120. Again, any suitable type of program can be used for displaying and manipulating the macromolecules, the coordinates of which are provided to the computer-graphics display system 116 by the CPU 102.

Design documentation and memos were written using PDL (Program Design Language) from Caine, Farber & Gordon of Pasadena, Calif. Again, any suitable type of program can be used for the design documents and memos.

Figure 2:
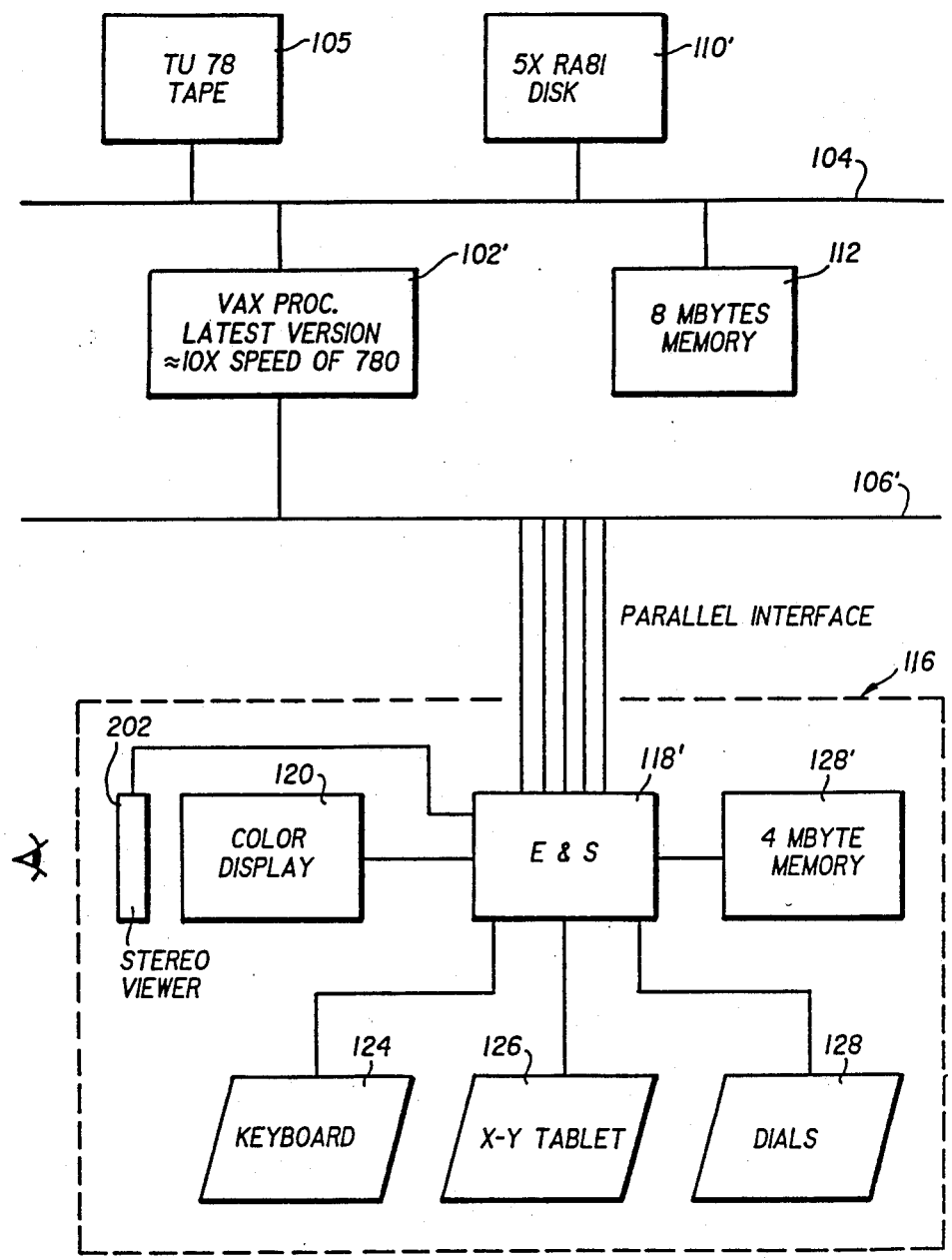
FIG. 2 is a block diagram of an alternate embodiment of the hardware aspects of the present invention.

FIG. 2 shows in block diagram for an improved version of the hardware system of the present invention. Like numbers refer to like items of FIG. 1. Only the differences between the serial processor mode system of FIG. 1 and the improved system of FIG. 2 are discussed below.

The CPU 102' is the latest version of the Vax 11/780 from Digital Equipment Corporation. The latest processor from DEC in the VAX product family is approximately ten times faster than the version shown in the serial processor mode of FIG. 1.

Instead of the two Rm05 disk drives 108 of FIG. 1, the embodiment of FIG. 2 utilizes five RA 81 disk drive units 110'. This is to upgrade the present system to more state of the art disk drive units, which provide greater storage capability and faster access.

Serial processor 106 is connected directly to the electronic stage 118' of the computer-graphics display system 116. The parallel interface in the embodiment of FIG. 2 replaces the serial interface approach of the serial processor mode of FIG. 1. This allows for faster interaction between CPU 102' and electronic stage 118' so as to provide faster data display to the expert operator.

Disposed in front of color display 120 is a stereo viewer 202. A suitable form for stereo viewer 202 is made by Terabit, Salt Lake City, Utah. Stereo viewer 202 would provide better 3-D perception to the expert operator than can be obtained presently through rotation of the molecule.

In addition, this embodiment replaces the Frodo macromolecule display programs with a program designed to show a series of related hypothetical molecules. This newer program performs the operations more uickly so that the related hypothetical molecules can be presented to the expert operator in a short enough time that makes examination less burdensome on the operator.

The programs can be modified so as to cause the present invention to eliminate candidates in the second general step where obvious rules have been violated by the structures that are produced. For example, one rule could be that if an atom in a linker comes closer than one Angstrom to an atom in the native structure the candidate would be automatically eliminated.

In addition, the surface accessibility of molecules could be determined and a score based on the hydrophobic residues in contact with the solvent could be determined. After the hydrophobic residues have been calculated, the candidates could be ranked so that undesired candidates could automatically be eliminated. The protein is modeled in the present invention without any surrounding matter. Proteins almost always exist in aqueous solution; indeed, protein crystals contain between 20% and 90% water and dissolved salts which fill the space between the protein molecules. Certain kinds of amino acids have sidechains which make favorable interactions with aqueous solutions (serine, threonine, arginine, lysine, histidine, aspartic acid, glutamic acid, proline, asparagine, and glutamine) and are termed hydrophylic. Other amino acids have side chains which are apolar and make unfavorable interactions with water (phenylalanine, tryptophan, leucine, isoleucine, valine, methionine, and tyrosine) and are termed hydrophobic. In natural proteins, hydrophylic amino acids are almost always found on the surface, in contact with solvent; hydrophobic amino acids are almost always inside the protein in contact with other hydrophobic amino acids. The remaining amino acids (alanine, glycine, and cycteine) are found both inside proteins and on their surfaces. The designs of the present invention should resemble natural proteins as much as possible, so hydrophobic residues are placed inside and hydrophilic residues are place outside as much as possible.

Programs could be utilized to calculate an energy for each hypothetical structure. In addition, programs could make local adjustments to the hypothetical molecules to minimize the energy. Finally, molecular dynamics could be used to identify particularly unstable parts of the hypothetical molecule. Although existing programs could calculate a nominal energy for each hypothetical structure, it has not yet been demonstrated that such calculations can differentiate between sequences which will fold and those that will not. Energy minimization could also be accomplished with extant programs, but energy minimization also can not differentiate between sequences which will fold and those that will not. Molecular dynamics simulations currently cannot be continued long enough to simulate the actual folding or unfolding of a protein and so cannot distinguish between stable and unstable molecules.

Two megabytes of storage 128' in the computer generated display system 116 is added so that several different molecules can be stored at the display level. These molecules then can be switched back and forth on the color display 120 so that the expert operator can sequentially view them while making expert decisions. The parallel interface that is shown in FIG. 2 would allow the coordinates to be transferred faster from the CPU 102' to the electronics stage 118' of the computer generated display system 116.

The parallel processing architecture embodiment of the present invention is described below in Section V. This parallel architecture embodiment provides even faster analysis and display.

III. Single Linker Embodiment

This first embodiment of the present invention determines and displays possible chemical structures for using a single linker to convert two naturally aggregated but chemically separate polypeptides chains into a single polypeptide chain which will fold into a three dimensional structure very similar to the original structure made of two polypeptide chains.

A Plausible Site Selection

Figure 3:
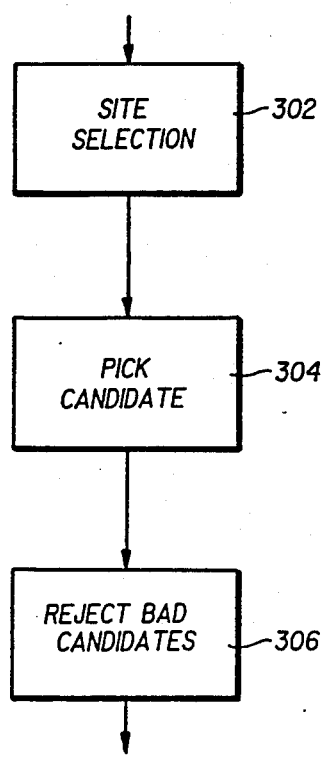
FIG. 3 is a block diagram of the three general steps of the present invention.

There are two main goals of the plausible site selection step 302 of the present invention shown in very generalized block diagram form in FIG. 3. The first goal is to select a first plausible site on the first chain that is the minimum distance from the second plausible site on the second chain. The first point on the first chain and the second point on the second chain comprise the plausible site.

The second goal of the site selection is to select plausible sites that will result in the least loss of native protein. Native protein is the original protein composed of two (or more) aggregated polypeptide chains. It is not chemically possible to convert two chains to one without altering some of the amino acids. Even if only one amino acid was added between the carboxy terminal of the first domain and the amino terminal of the second domain, the charges normally present at these terminii would be lost. In most proteins containing two or more chains, the terminii are not very close together. Hypothetical linkers which join the carboxy terminus of one chain to the amino terminus of the other do not resemble natural protein structures. Although such structures are not impossible, it seems more reasonable to cut away small parts of the native protein so that compact linkers which resemble natural protein will span the gap. Many natural proteins are known to retain their structure when one or more residues are removed from either end.

Figure 4:
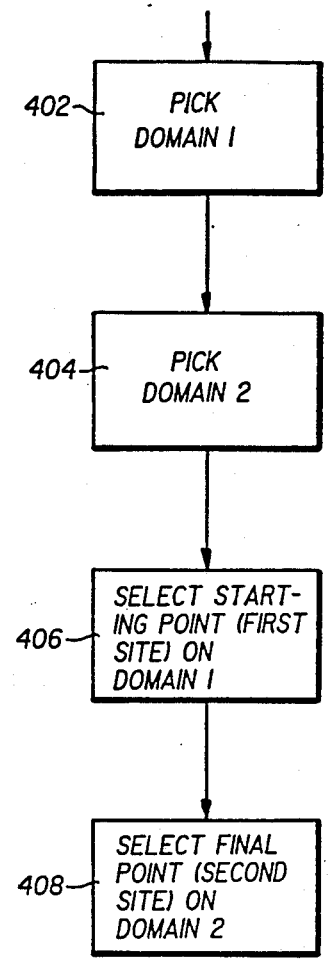
FIG. 4 is a block diagram of the steps in the site selection step in the single linker embodiment.

In the present embodiment, only a single linker (amino acid sequence or bridge for bridging or linking the two plausible sites to form a single polypeptide chain) is used. FIG. 4 shows in block diagram form the steps used to select plausible sites in the single linker. The steps of FIG. 4 are a preferred embodiment of step 302 of FIG. 3.

A domain 1 is picked in a step 402 (see FIG. 4). A schematic diagram of two naturally aggregated but chemically separate polypeptide chains is shown in FIG. 5A. For purposes of illustration, assume that L is the light chain of an antibody variable region (the first polypeptide chain) and is domain 1. As shown in FIG. 5A, light chain L is on the left side, and the variable region of the heavy chain H is on the right side.

The next step 404 is to pick the domain 2, which, as indicated, is the heavy chain variable region H on the right side of FIGS. 5A and 5B.

The linker that will be selected will go from domain 1 (the light chain L) towards domain 2 (heavy chain H).

Figure 6A:
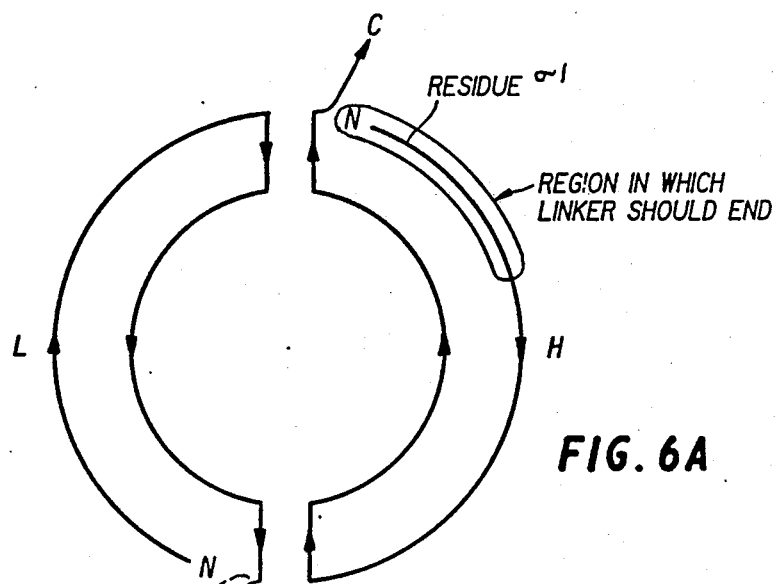
FIG. 6A is a simplified two dimensional schematic diagram of the two polypeptide chains showing the location of the residue Tau 1 and the residue Sigma 1. of FIG. 6B is a two dimensional representation the actual relationship of the two polypeptide chains showing the residue Tau1 and the residue Sigma1.
Figure 6B:
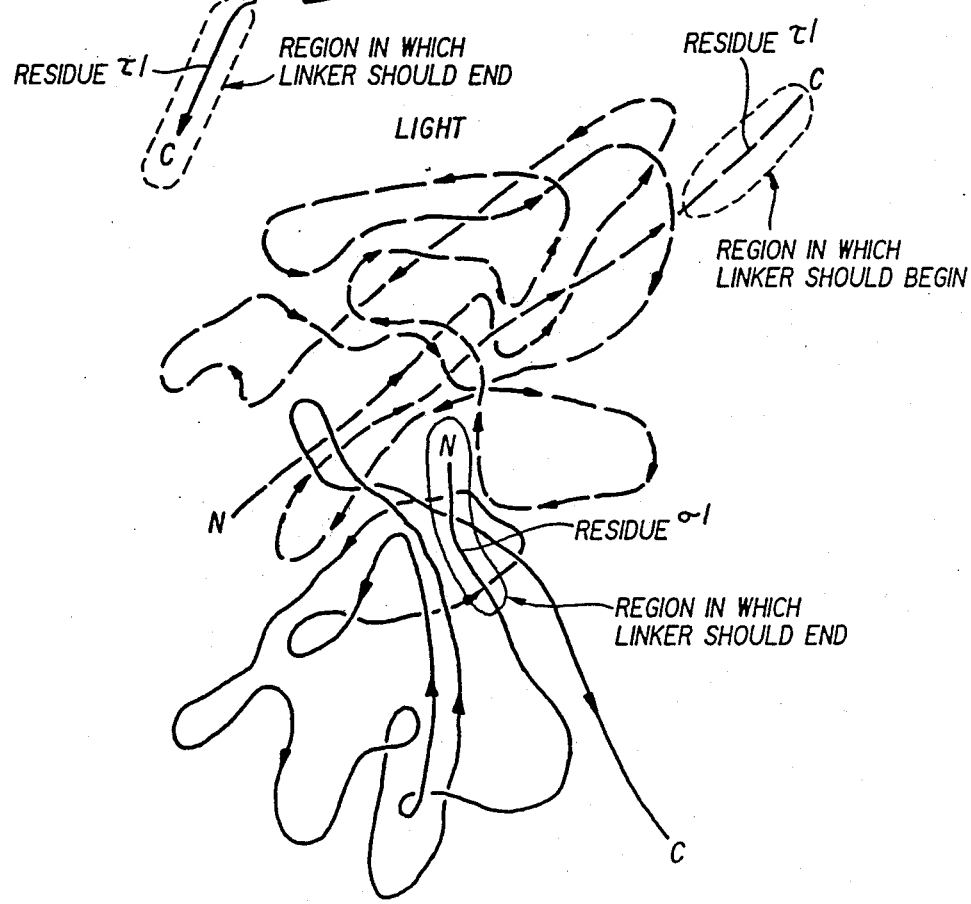

As the linker will become part of the single polypeptide chain, it must have the same directionality as the polypeptides it is linking; i.e. the amino end of the linker must join the carboxy terminal of some amino acid in domain 1 and the carboxy terminal of the linker must join the amino terminal of some residue in domain 2. A starting point (first site) on domain 1 is selected, as represented by step in 406 in FIG. 4. The starting point is chosen to be close to the C (C for carboxy) terminal of domain 1, call this amino acid tau 1. It is important to pick tau 1 close to the C terminal to minimize loss of native protein structure. Residue tau 1 is shown schematically in two dimensions in FIG. 6A; it is also shown in FIG. 6B where it is presented in a two-dimensional representation of the naturally aggregated but chemically separate polypeptide chains.

Next, the final point (second site) close the N (N for amino) terminal of domain 2 is selected, as indicated by step 408 of FIG. 4. The final site is an amino acid of domain 2 which will be called sigma 1. It is important that amino acid sigma 1 be close to the N terminal of domain 2 to minimize loss of native protein structure. Amino acid siqma 1 is shown schematically in FIG. 6A and in the more realistic representation of FIG. 6B.

Figure 7:
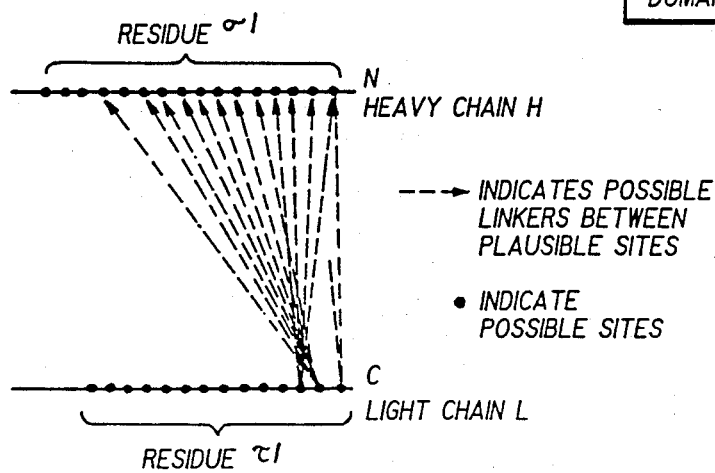
FIG. 7 shows in very simplified schematic way the concept of the direction linkers that are possible between the various possible sites on the light chain L and the heavy chain H in the residue Tau 1 and residue Sigma 1 respectively.

FIG. 7 shows in simplified form the concept that the linker goes from a first site at amino acid tau 1 in domain 1 to a second site at amino acid sigma 1 in domain 2. There are a plurality of possible first sites and a plurality of second sites, as is shown in FIG. 7. A computer program prepares a table which contains for each amino acid in domain 1 the identity of the closest amino acid in domain 2 and the distance. This program uses the position of the aloha carbon as the position of the entire amino acid. The expert operator prepares a list of plausible amino acids in domain 1 to be the first site, tau 1, and a list of plausible amino acids in domain 2 to be the second site, sigma 1. Linkers are sought from all plausible sites tau 1 to all plausible sites siqma 1. The expert operator must exercise judgment in selecting the sites tau 1 and siqma 1 in deciding that certain amino acids are more important to the stability of the native protein than are other amino acids. Thus the operator may select sites which are not actually the closest.

The complete designed polypeptide chain in accordance with the present invention consists of the domain 1 (of the light chain L) up to the amino acid tau 1, the linker, as shown by the directional-line in FIG. 8A and in FIG. 8B, and the domain 2 from amino acid sigma 1 to the C terminus of the heavy chain, H. As shown in FIGS. 8A and 8B, in the representative example, this results in the following loss of native protein.

The first loss in native protein is from the residue after residue tau 1 to the C terminus of domain 1 (light chain L). The second loss of native protein is from the N terminus of domain 2 (heavy chain H) to the amino acid before sigma 1.

As is best understood from FIG. 8A, the introduction of linker 1 produces a single polypeptide chain from the two naturally aggregated chains. The polypeptide chain begins with the N terminal of domain 1. Referring now to FIG. 8B, the chain proceeds through almost the entire course of the native light chain, L, until it reaches amino acid tau 1. The linker then connects the carboxy terminal of a very slightly truncated domain 1 to residue sigma 1 in the very slightly truncated domain 2. Since a minimum amount of native protein is eliminated, and the liner is selected to fit structurally as well as possible (as described below in connection with general steps 2 and 3 of the present invention), the resulting single polypeptide chain has a very high probability (several orders of magnitude greater than if the linker was selected randomly) to fold into a three-dimensional structure very similar to the original structure made of two polypeptide chains.

The single polypeptide chain results in a much more stable protein which can be expressed genetically in one step. In this way a single polypeptide chain can be engineered from the naturally occuring two-polypeptide chain native protein so as to create a polypeptide of only one chain, but maintaining the binding site, or any other original biological function.

In the current mode of the present invention, the expert operator selects the sites with minimal help from the computer. The computer prepares the table of closest-residue-in-other-domain. The computer can provide more help in the following ways.

(1) Prepare a list of conserved and variable residues for variable regions of antibodies (Fv region). Residues which vary from Fv to Fv would be much better starting or ending sites for linkage than are residues which are conserved over many different Fv sequences.

(2) Prepare a list of solvent accesibilities. Amino acids exposed to solvent can be substituted with less likelihood of destabilizing the native structure than amino acids buried within the native structure. Exposed amino acids are better choices as start or end of linkages.

With respect to each of the plurality of possible first sites (on domain 1 or light chain, L) there are available a plurality of second sites (on domain 2 or heavy chain H). As the second site is selected closer to the N terminus of doman 2, the distance to any of the plausible first sites increases. Also, as the first site is selected closer to the C terminus of domain 1 the distance to any of the plausible second sites increases. It is this tension between shortness of linker and retention of native protein which the expert operator resolves in choosing gaps to be linked. The penalty for including extra sites in the list of gaps are:

(1) searching in general step 2 will be slower; and
(2) more candidates will pass from step 2, many of which must be rejected in step 3. As step 3 is currently a manual step, this is the more serious penalty.

FIG. 8B shows diagramatically by a directional arrow the possible links that can occur between the various sites near the C terminal of domain 1 and the various sites near the N terminal of domain 2.

B. Selection of Candidates

In the second of the three general steps of the present invention as used in the single linker embodiment, plausible candidates for linking the site 1 on domain 1 with site 2 on domain 2 are selected from a much larger group of candidates. This process of winnowing out candidates results in the expert operator and/or expert system having a relatively small group of candidates to rank from most plausible to least plausible in the third general step of the present invention, as described in subsection C below.

Currently, there are approximately 250 protein structures, determined at 2.0A (angstrom) or higher resolution, in the public domain. The structures of these very complicated molecules are determined using sophisticated scientific techniques such as X-ray crystallography, neutron diffraction, and nuclear magnetic resonance. Structure determination produces a file of data for each protein. The Brookhaven Protein Data Bank (BPDB) exemplifies a repository of protein structural information. Each file in BPDB contains many records of different types. These records carry the following information:

(1) Name of the protein and standard classification number, (2) Organism from which protein was obtained, (3) Name and address of contributor, (4) Amino-acid sequence of each polypeptide chain, if known, (5) Connectivity of disulfides, if any, (6) Names and connectivities of any prosthetic groups, if any, (7) References to literature, (8) Transformation from reported coordinates to crystallographic coordinates, (9) Coordinates of each atom determined.

There is at least one record for each atom for which a coordinate was determined. Some parts of some proteins are disordered and do not diffract X-rays, so no sensible coordinates can be given. Thus there may be amino acids in the sequence for which only some or none of the atoms have coordinates. Coordinates are given in Angstrom units (100,000,000A = 1 cm) on a rectangular Cartesian grid. As some parts of a protein may adopt more than one spatial configuration, there may be two or more coordinates for some atoms. In such cases, fractional occupancies are given for each alternative position. Atoms move about, some more freely than others. X-ray data can give an estimate of atomic motion which is reported as a temperature (a.k.a. Debye-Waller) factor.

Any other data base which included, implicitly or explicitly, the following data would be equally useful:

(1) Amino acid sequence of each polypeptide chain.

(2) Connectivity of disulfides, if any, (3) Names and connectivities of any prosthetic groups, if any, (4) Coordinates (x, y, z) of each atom in each observed configuration.

(5) Fractional occupancy of each atom, (6) Temperature factor of each atom.

Proteins usually exist in aqueous solution. Although protein coordinates are almost always determined for proteins in crystals, direct contacts between proteins are quite rare. protein crystals contain from 20% to 90% water by volume. Thus one usually assumes that the structure of the protein in solution will be the same as that in the crystal. It is now generally accepted that the solution structure of a protein will differ from the crystal structure only in minor details. Thus, given the coordinates of the atoms, one can calculate quite easily the solvent accessibility of each atom.

In addition, the coordinates implicitly give the charge distribution throughout the protein. This is of use in estimating whether a hypothetical molecule (made of native protein and one or more linkers) will fold as designed. The typical protein whose structure is known comprises a chain of amino acids (there are 20 types of amino acids) in the range of 100 to 300 amino acids.

Each of these amino acids alone or in combination with the other amino acids as found in the known protein molecule can be used as a fragment to bridge the two sites. The reason that known protein molecules are used is to be able to use known protein fragments for the linker or bridge.

Even with only 250 proteins of known structure, the number of possible known fragments is very large. A linker can be from one to twenty or thirty amino acids long. Let "Lmax" be the maximum number of amino acids allowed in a linker, for example, Lmax might be 25. Consider a protein of "Naa" amino acids. Proteins have Naa in the range 100 to 800, 250 is typical. From this protein, one can select Naa—1 distinct two-amino-acid linkers, Naa—2 distinct three-amino-acid linkers, . . . and (Naa+1—Lmax) distinct linkers containing exactly Lmax amino acids. The total number of linkers containing Lmax or fewer linkers is "Nlink,"

$$Nlink = \sum_{j=1,Lmax} (Naa + 1 - j)$$
$$= Naa \times (Lmax) - (Lmax \times Lmax)/2 + Lmax/2$$

If Naa is 250 and Lmax is 25, Nlink will be 5975. If the number of known proteins is "Nprot," then the total number of linkers, "Nlink total" will be $$Nlink\_total = \sum_{k=1,Nprot} \sum_{j=1,Lmax} (Naa(k) + 1 - j)$$
$$= \sum_{k=1,Nprot} [Naa(k) \times (Lmax) - (Lmax \times Lmax)/2 + Lmax/2]$$
$$= Nprot \times (Lmax/2 - Lmax \times Lmax)/2 + Lmax \sum_{K=1,Nprot} Naa(k)$$

Where Naa(k) is the number of amino acids in the kth protein. With 250 proteins, each containing 250 amino acids (on average), and Lmax set to 25, Nlink total is 1,425,000.

This is the number of linkers of known structure. If one considers the number of possible amino acid sequences up to length Lmax (call it "Nlink possible"), it is much larger.

$$Nlink\_possible = \sum_{J=1,Lmax} 20^J$$

For Lmax = 25
Nlink possible = 353, 204, 547, 368, 421, 052, 631, 578, $$947, 368, 420 = 3.53 * 10^{32}$$

Using known peptide fragments thus reduces the possibilities by twenty-six orders of magnitude. Appropriate searching through the known peptide fragments reduces the possibilities a further five orders of magnitude.

Essentially, the present invention utilizes a selection strategy for reducing a list of possible candidates. This is done as explained below in a preferred form in a three step process. This three step process, as is illustrated in the explanation of the each of the three steps of the process, significantly reduces the computer time required to extract the most promising candidates from the data base of possible candidates. This should be contrasted with a serial search throughout the entire data base of candidates, which would require all candidates to be examined in total. The present invention examines certain specific parameters of each candidate, and uses these parameters to produce subgroups of candidates that are then examined by using other parameters. In this way, the computer processing speed is significantly increased.

The best mode of the present invention uses a protein data base created and supplemented by the Brookhaven National Laboratory in Upton, Long Island, N.Y. This data base is called the Brookhaven Protein Data Bank (BPDB). It provides the needed physical and chemical parameters that are needed by the present invention. It should be understood, that the candidate linkers can be taken from the Brookhaven Protein Data Bank or any other source of three-dimensional protein structures. These sources must accurately represent the proteins. In the current embodiment, X-ray structures determined at resolution of 2.5A or higher and appropriately refined were used. Each peptide is replaced (by least-squares fit) by a standard planar peptide with standard bond lengths and angles. Peptides which do not accurately match a standard peptide (e.g. cis peptides) are not used to begin or end linkers, but may appear in the middle.

Each sequence up to some maximum number of amino acids (Lmax) is taken as a candidate. In the preferred embodiment, the maximum number of amino acids (Lmax) is set to 30. However, the present invention is not limited to this number, but can use any maximum number that is desired under the protein engineering circumstances involved.

1. Selectinq Candidates with Proper Distance Between the N Terminal and the C Terminal.

The first step in the selection of candidates step is to select the candidate linkers with a proper distance between the N terminal and the C terminal from all of the candidate linkers that exist in the protein data base that is being used. FIG. 9 shows in block diagram form the steps that make up this candidate selection process utilizing distance as the selection parameter.

Referring to FIG. 9, a standard point relative to the peptide unit at the first site is selected, as shown by block 902.

A standard point relative to the peptide unit in the second site is also picked, as indicated by a block 904. Note that in the best mode the geometric centers of the peptide units of the first and second sites are used, but any other standard point can be utilized, if desired.

The distance between the standard points of the two peptides at the first and second sites defining the gap to be bridged by the linker is then calculated, as indicated by block 906. This scalar distance value is called the Span of the gap. Note that this scalar value does not include any directional information.

Next, as indicated by a step 908, the distance between the ends of the possible linker candidates are calculated. The distance between the ends of a particular candidate is called the span of the candidate. Note that each possible linker candidate has a span of the candidate scalar value.

The final step in the distance selection candidate selection process is that of a step 910. In step 910, candidates are discarded whose span of the candidate values differ from the span of the gap value by more than a preselected amount (this preselected amount is Max LSQFIT error). In the best mode of the present invention, the preselected amount for Max LSQFIT error is 0.50 Angstroms. However, any other suitable value can be used.

The expert user often selects several gaps and the search uses all of them. The span of each candidate is compared to the span of each gap until it matches one, within the preset tolerance, or the list of gaps is exhausted. If the candidate matches none of the gaps, it is discarded. If it matches any gap it is carried to the next stage.

The inventor has determined that the use of the distance as the first parameter for discarding possible linker candidates results in a significant reduction in the number of possible candidates with a minimum amount of computer time that is needed. In terms of the amount of reduction, a representative example (using linkers up to 20 amino acids) starts out with 761,905 possible candidates that are in the protein data base. This selection of candidates using the proper distance parameter winnows this number down to approximately 63,727 possible candidates. As is discussed below, the distance selection operation requires much less computer time than is required by the other two steps which make up this selection step 304.

The result of this selection of candidates according to proper distance is a group (called a first group of candidates) which exhibit a proper length as compared to the gap that is to be bridged or linked. This first group of candidates is derived from the protein data base using the distance criteria only.

2. Selecting Candidates with Proper Direction from N Terminal to C Terminal

This substep essentially creates a second group of possible candidates from the first group of possible candidates which was produced by the distance selection substep discussed in connection with FIG. 9. The second group of candidates is selected in accordance with the orientation of the C terminal residue (i.e. the final residue) of the linker with respect to the N terminal residue (i.e. the initial residue) which is compared to the orientation of the C terminal residue (i.e. the second site) of the gap with respect to the N terminal residue (i.e. the first site). See FIG. 20B. In this way, this direction evaluation determines if the chain of the linker ends near the second site of the gap, when the amino terminal amino acid of the linker is superimposed on the first site of the gap so as to produce the minimum amount of unwanted molecular distortion.

Referring now to FIG. 10, the first step used in producing the second group of possible candidates is a step 1002. In step 1002 a local coordinate system is established on the N terminal residue of one of the selected gaps. For example, one might take the local X-axis as running from the first alpha carbon of the N terminal residue to the second alpha carbon of the N terminal residue, with the first alpha carbon at the origin the second alpha carbon on the plus X-axis. The local Y-axis is selected so that the carbonyl oxygen lies in the xy plane with a positive y coordinate. The local Z-axis is generated by crossing X into Y. Next, as indicated by step 1004, a standard reference point in the C terminal residue of the gap is located and its spherical polar coordinates are calculated in the local system. The standard reference point could be any of the atoms in the C terminal peptide (throughout this application, peptide, residue, and amino acid are used interchangeably) or an average of their positions. Steps 1002 and 1004 are repeated for all gaps in the list of gaps. As indicated by step 1006, a local coordinate system is established on the N terminal residue of one of the candidates. This local coordinate system must be established in the same manner used for the local coordinate systems established on each of the gaps. Various local systems could be used, but one must use the same definition throughout. In step 1008, the standard reference point is found in the C terminal residue of the current candidate. This standard point must be chosen in the same manner used for the gaps. The spherical polar coordinates of the standard point are calculated in the local system of the candidate. (This use of local coordinate system is completely equivalent to rotating and translating all gaps and all candidates so that their initial peptide lies in a standard position at the origin.) In step 1010, the spherical polar coordinates of the gap vector (r, theta, phi) are compared to the spherical polar coordinates of the candidate vector (r, theta, phi). In step 1012 a preset threshhold is applied, if the two vectors agree closely enough, then one proceeds to step 1014 and enrolls the candidate in the second group of candidates. Currently, this preset threshhold is set to 0.5A, but other values could be used. From step 1014, one skips forward to step 1022, vide infra. On the other hand, if the vectors compared in step 1012 are not close enough, one moves to the next gap vector in the list, in step 1016. If there are no more gaps, one goes to step 1018 where the candidate is rejected. If there are more gaps, step 1020 increments the gap counter and one returns to step 1010. From steps 1014 or 1018 one comes to step 1022 where one tests to see if all candidates have been examined. If not, step 1024 increments the candidate counter and one returns to step 1006. If all candidates have been examined, one has finished, step 1026.

FIGS. 11A–11C the concept of comparing the direction of the gap to the direction of the candidate.

The inventor has determined that in the example discussed above where 761,905 possible candidates are in the protein data base, the winnowing process in this step reduces the approximate 63,727 candidates in the first group to approximately 50 candidates in the second group. The inventor has also determined that as referenced to the units of computer time referred to above in connection with the scalar distance parameter, it takes approximately 4 to 5 computer units of time to perform the selection of this step. Thus, it can be appreciated that it preserves computer time to perform the distance selection first, and the direction selection second since the direction selection process takes more time than the distance selection process.

3. Selecting Candidates with Proper Orientation at Both Termini

In this step, the candidates in the second group of step 1016 of FIG. 10 are winnowed down to produce a third group of plausible candidates using an evaluation of the relative orientation between the peptide groups at either end of the candidate, compared to the relative orientation between the peptide groups at either end of the gap. In a step 1201, (FIG. 12) decide that a peptide will be represented by 3, 4, or 5 atoms (vide infra). Specifically, in a step 1202, one of the candidates in the second group (step 1014) is selected for testing. In a step 1204, three to five atoms in the first peptide are selected to define the orientation of the first peptide. So long as the atoms are not collinear, three atoms is enough, but using four or five atoms makes the least-squares procedure which follows over-determined and therefore compensates for errors in the coordinates. For example, assume selection of four atoms: Calpha, C, N, and Calpha. Next, in a step 1206, one selects the corresponding 3,4, or 5 atoms from the final peptide of the selected candidate. These 6, 8, or 10 atoms define a three-dimensional object. In a step 1208, select one of the gaps. Select the corresponding 6, 8 or 10 atoms from the gap. In a step 1210, least-squares fit the atoms from the candidate to the atoms from the gap. This least-squares fit allows degrees of freedom to superimpose the two three-dimensional objects. Assume that one object is fixed and the other is free to move. Three degrees of freedom control the movement of the center of the free object. Three other degrees of freedom control the orientation of the free object. In a step 1212, the result of the least-square fit is examined. If the Root-Mean-Square (RMS) error is less than some preset threshhold, the the candidate is a good fit for the gap being considered and is enrolled in the third group in a step 1214. If, on the other hand, the RMS error is greater than the preset threshhold, one checks to see if there is another gap in the list in a step 1216. If there is, one selects the next gap and returns to step 1208. If there are no more gaps in the list, then the current candidate from the second group is rejected in step 1218. In step 1220, one checks to see if there are more candidates in the second group; if so, a new candidate is selected and one returns to step 1201. If there are no more candidates, one is finished (step 1222). Again referring to a representative case, where linkers of length up to twenty amino acids were sought for a single gap with separation 12.7A, the protein data bank contained 761,905 potential linkers. Of these, 63,727 passed the distance test. The direction test removed all but 50 candidates. The orientation test passed only 1 candidate with RMS error less than or equal to 0.5A. There were two additional candidates with RMS error between 0.5A and 0.6A. Moreover, the inventors have determined that it takes about 25 units of computer time to evaluate each candidate in group 2 to decide whether they should be selected for group 3. It can be appreciated now that the order selected by the inventors for the three steps of winnowing the candidates has been selected so that the early steps take less time per candidate than the following steps. The order of the steps used to select the candidate can be changed, however, and still produce the desired winnowing process. Logically, one might even omit steps one and two and pass all candidates through the least-squares process depicted in FIG. 12 and achieve the same list of candidates, but at greater cost in computing. This may be done in the case of parallel processing where computer time is plentiful, but memory is in short supply.

Another approach (not illustrated) for determining whether the proper orientation exists between the ends of the candidate, is to examine only the atoms at the C terminal of the candidate as compared to the atoms at the final peptide of the gap. In step 2, the inventors aligned the first peptide of the candidate with the first peptide in the gap. Having done this, one could merely compare the atoms at the C terminal of the candidate with the atoms of the second peptide of the gap. This approach is inferior to that discussed above because all the error appears at the C terminus, while the least-squares method discussed above distributes the errors evenly.

C. Ranking and Eliminating Candidates.

As shown in FIG. 3, the third general step in the present invention is that of ranking the plausible candidates from most plausible to least plausible, and eliminating those candidates that do not appear to be plausible based on criteria utilized by an expert operator and/or expert system.

In the best mode, the candidates in the third group (step 1214) are provided to the expert operator, who can sequentially display them in three dimensions utilizing the computer-graphics display system 116. The expert operator then can make decisions about the candidates based on knowledge concerning protein chemistry and the physical relationship of the plausible candidate with respect to the gap being bridged. This analysis can be used to rank the plausible candidates in the third group from most plausible to least plausible. Based on these rankings, the most plausible candidates can be selected for genetic engineering.

As noted above in connection with the illustrative example, there are typically few (under 100) candidates which make it to the third group of step 1214. Consequently, a moderately expert operator (one having a Bachelor of Science degree in chemistry, for example), can typically winnow down this number of plausible candidates to a group of 10 to 15. Thereafter, a more expert operator and/or expert system can further winnow down the number. In this way, only a very few of the plausible candidates needs to be tested in practice as compared to the hundreds, thousands or more of candidates that would have to be tested if no selection process like that of the present invention was used. This speeds up the process of engineering the single chain molecules by orders of magnitude, while reducing costs and other detriments by orders of magnitude as well.

In certain situations, however, automatic ranking in this third general step may be warranted. This could occur, for example, where the expert operator was presented with quite a few candidates in the third group, or where it is desired to assist the expert operator in making the ranking selections and eliminating candidates based on prior experience that has been derived from previous engineering activities and/or actual genetic engineering experiments.

Referring now to FIG. 13, a coordinate listing of the hypothetical molecule (candidate) is automatically constructed, as is indicated by a block 1302. The expert operator can then display using a first color the residues from domain 1 of the native protein. Color display 120 can provide a visual indication to the expert operator of where the residues lie in domain 1. This is indicated by a block 1304.

The expert operator then can display on color display 120 the residues from domain 2 of the native protein using a second color, as is indicated by a block 1306. The use of a second color provides a visual indication to the user which assists in distinguishing the residues from domain 1 from the residues from domain 2.

The linker (candidate) being ranked can be displayed in a selected color, which color can be different from the first color of step 1304 and/or the second color from step 1306. Again, by using this visual color indication, the expert operator can distinguish the residues of domain 1 and 2 of the native protein. This display of the linker candidate is indicated by a block 1308.

The initial picture on the color display 120 provided to the expert operator typically shows the alpha carbons for all of the residues. This is indicated by a block 1310. In addition, the initial picture shows the main-chain and side-chains for residues and linkers and one residue before the linker and one residue after the linker. This is indicated by a block 1312.

The expert operator can also cause any of the other atoms in the native protein or linker candidate to be drawn at will. The molecule can be rotated, translated, and enlarged or reduced, by operator command, as was discussed generally in connection with the computer-graphics display system 116 above. The block diagram of FIG. 13 indicates that each of the steps just discussed are accomplished in serial fashion. However, this is only for purposes of illustration. It should be understood that the operator can accomplish any one or more of these steps as well as other steps at will and in any sequence that is desired in connection with the ranking of the plausible candidates in group 3.

The expert operator and/or expert system utilized in this third general step in ranking the candidates from most plausible to least plausible and in eliminating the remaining candidates from group 3, can use a number of different rules or guidelines in this selection process. Representative of these rules and guidelines are the following which are discussed in connection with FIG. 14. Note that the blocks in FIG. 14 show the various rules and/or criteria, which are not necessarily utilized in the order in which the boxes appear. The order shown is only for purposes of illustration. Other rules and/or criteria can be utilized in the ranking process, as well.

As shown in step 1402, a candidate can e rejected if any atom of the linker comes closer than a minimum allowed separation to any retained atom of the native protein structure. In the best mode, the minimum allowed separation is set at 2.0 Angstroms. Note that any other value can be selected. This step can be automated, if desired, so that the expert operator does not have to manually perform this elimination process.

A candidate can be penalized if the hydrophobic residues have high exposure to solvent, as is indicated by a block 1404. The side chains of phenylananine, tryptophan, tyrosine, leucine, isoleucine, methionine, and valine do not interact favorably with water and are called hydrophobic. Proteins normally exist in saline aqueous solution; the solvent consists of polar molecules ($H_2O$) and ions.

A candidate can be penalized when the hydrophilic residues have low exposure to solvent. The side chains of serine, threonine, aspartic acid, glutamic acid, asparagine, glutamine, lysine, arginine, and proline do interact favorably with water and are called hydrophilic. This penalization step for hydrophilic residues is indicated by a block 1406.

A candidate can be promoted when hydrophobic residues have low exposure to solvent, as is indicated by a block 1408.

A candidate can be promoted when hydrophilic residues have high exposure to solvent, as indicated by a block 1410.

A candidate can be penalized when the main chain fails to form hydrogen bonds, as is indicated by a block 1412.

A candidate can be penalized when the main chain makes useless excursions into the solvent region. Useless excursions are those which do not make any evident interaction with the retained native protein. This is indicated by a block 1414.

A candidate can be promoted when th main chain forms a helix, as is indicated by a block 1416. Hilices are self-stabilizing. Thus a linker which is helical will be more stable because its main-chain polar atoms (O and N) will form hydrogen bonds within the linker.

As is indicated by a block 1418, a candidate can be promoted when the main chain forms a beta sheet which fits against existing beta sheets. The strands of beta sheets stabilize each other. If a linker were found which was in a beta-sheet conformation such that it would extend an existing beta sheet, this interaction would stabilize both the linker and the native protein.

Another expert design rule penalizes candidates which have sterically bulky side chains at undesirable positions along the main chain. Furthermore, it is possible to "save" a candidate with a bulky side chain by replacing the bulky side chain by a less bulky one. For example if a side chain carries a bulky substituent such as leucine or isoleucine, a possible design step replaces this amino acid by a glycine, which is the least bulky side chain.

Other rules and/or criteria can be utilized in the selection process of the third general step 306, and the present invention is not limited to the rules and/or criteria discussed. For example, once the linker has been selected it is also possible to add, delete, or as stated, modify one or more amino acids therein, in order to accomplish an even better 3-D fit.

IV. Double and Multiple Linker Embodiments

Section III above described the single linker embodiment in accordance with the present invention. This section describes double linker and multiple linker embodiments in accordance with the present invention. For brevity purposes, only the significant differences between this embodiment and the single linker embodiment will be described here and/or illustrated in separate figures. Reference should therefore be made to the text and figures that are associated with the single linker embodiment

A. Plausible Site Selection.

The two main goals of minimizing distance between the sites to be linked and the least loss of native protein apply in the site selection in the double and multiple linker embodiments as they did apply in the single linker embodiment discussed above.

FIG. 15A shows a simplified two dimensional representation of the use of two linkers to create the single polypeptide chain from the two naturally aggregated but chemically separate polypeptide chains. FIG. 15B shows in two dimensions a three dimensional representation of the two chains of FIG. 15A. Referring now to FIGS. 15A and B, the first step in determining suitable sites is to find a site in domain 1 which is close to either the C or N terminus of domain 2. For purposes of illustration, and as is shown in FIGS. 15A and 15B, it is assumed that the most promising location is the C terminus of domain 2. The residue in domain 1 is called Tau 1, while the residue in domain 2 is called Sigma 1.

FIGS. 16A and 16B are respectively two dimensional simplified plots of the two chains, and two dimensional plots of the three dimensional representation of the two chains. They are used in connection with the explanation of how plausible sites are selected for the second linker in the example situation.

The first step in connection with finding plausible sites for the second linker is to find a residue in domain 1 that is before Tau 1 in the light chain. This residue is called residue Tau 2. It is shown in the top portion in FIG. 16A, and in the right middle portion in FIG. 16B.

The next step in the site selection process for the second linker is to find a residue in domain 2 near the N terminus of domain 2. This residue is called residue Sigma 2. Reference again is made to FIGS. 16A and B to show the location of Sigma 2.

The second linker (linker 2) thus runs from Tau 2 to Sigma 2. This is shown in FIGS. 17A and 17B. Note that the chain that is formed by these two linkers has the proper direction throughout.

FIG. 18 shows in two dimensional simplified form the single polypeptide chain that has been formed by the linking of the two independent chains using the two linkers. Note that the approach outlined above resulted in the minimal loss of native protein. The completely designed protein is shown in FIG. 17 and consists of domain 1 from the N terminal to Tau 2, linker 2, domain 2 from Sigma 2 to Sigma 1, linker 1, and domain 1 from Tau1 to the C terminus. The arrows that are shown in FIG. 17 indicate the direction of the chain.

FIGS. 17 A&B show that the residues lost by the utilization of the two linkers are: (a) from the N terminus of domain 2 up to the residue before Sigma 2; and (b) from the residue after Sigma 1 to the C terminus of domain 2; and (c) from the residue after Tau 2 to the residue before Tau 1 of domain 1.

If one of the linkers in the two linker case is very long, one could link from Tau 2 to a residue in domain 2 after Siqma 1. A third linker (not shown) would then be sought from a residue near the C terminal of domain 2 to a residue near the N terminal of domain 2.

Additionally, one could use two linkers to reconnect one of the domains in such a way that a single linker or a pair of linkers would weld the two domains into one chain.

B. Candidate Selection and Candidate Rejection Steps

Ranking of linkers in the multilinker cases follows the same steps as in the single linker case except there are some additional considerations.

(1) There may be a plurality of linkers for each of the two (or more) gaps to be closed. One must consider all combinations of each of the linkers for gap A with each of the linkers for gap B.

(2) One must consider the interactions between linkers.

As one must consider combinations of linkers, the ranking of individual linkers is used to cut down to a small nuber of very promising linkers for each gap. If one has only three candidates for each gap, there are nine possible constructs.

The process of examining interactions between linkers and discarding poor candidates can be automated by applying the rules discussed above.

Parallel Processing Embodiment

FIG. 19 shows in block diagram form the parallel processing approach that can be utilized in the present invention.

As shown in FIG. 19, a friendly serial processor 1902 is connected by a first bus 1904 to a plurality of data storage devices and input devices. Specifically, and only for purposes of illustration, a tape input stage 1906 is connected to bus 1904 so as to read into the system the parameters of the protein data base that is used. A high storage disk drive system 1908 (having, for example, 5 gigabits of storage) is also connected to bus 1904. Operationally, for even larger storage capabilities, an optical disk storage stage 1910 of conventional design can be connected to bus 1904.

The goal of the hypercube 1912 that is connected to the friendly serial processor 1902 via a bi-directional bus 1914 is twofold: to perform searching faster and to throw out candidates more automatically.

The hypercube 1912, having for example, $2^{10}$ to $2^{16}$ nodes provides for parallel processing. There are computers currently available which have up to 1,024 computing nodes. Thus each node would need to hold only about 1400 candidate linkers and local memory of available machines would be sufficient. This is the concept of the hypercube 1912. Using the hypercube parallel processing approach, the protein data base can be divided into as many parts as there are computing nodes. Each node is assigned to a particular known protein structure.

The geometry of the gap that has to be bridged by a linker is sent by the friendly serial processor 1902 via bus 1914 to the hypercube stage 1912. Each of the nodes in the hypercube 1912 then proceses the geometrical parameters with respect to the particular candidate linker to which it is assigned. Thus, all of the candidates can be examined in a parallel fashion, as opposed o the serial fashion that is done in the present mode of the present invention. This results in much faster location (the inventors believe that the processing speed can be brought down from 6 hours to 3 minutes using conventional technology) in locating the candidates that can be evaluated by the second step 304 of the present invention.

Another advantage for the parallel processing embodiment is that it will provide sufficient speed to allow candidates to be thrown out more automatically. This would be achieved using molecular dynamics and energy minimization. While this could be done currently on serial processing computers (of the super computer variety such as those manufactured by Cray and Cyber), the parallel processing approach will perform the molecular dynamics and energy minimization much faster and cheaper than using the super computing approach In particular, hypercube computers exist which have inexpensive computing nodes which compare very favorably to supercomputers for scalar arithmetic. Molecular dynamics and energy minimization are only partly vectorizable because the potential functions used have numerous data-dependent branches.

It should be understood that the examples presented above are merely for purposes of illustration. The scope of the present invention should therefore be interpreted by the following claims as defined by the foregoing figures and text.

I claim:

1. A computer based method, comprising the steps of:
   (a) providing a first polypeptide and a second polypeptide;
   (b) selecting, using computer methods, a first site on said first polypeptide, and a second site on said second polypeptide which are possible joining locations for a linker;
   (c) selecting possible linkers, using computer methods, for bridging from said first polypeptide at said first site to said second polypeptide at said second site; and
   (d) visually displaying, using computer graphics, computer-designed protein molecules, each comprising a portion of said first polypeptide, a portion of said second polypeptide, and one of said possible linkers selected by said step (c).

2. The method of claim 1, wherein said first and second polypeptides correspond to variable light and variable heavy portions of an antibody.

3. A computer based method for linking a first polypeptide and a second polypeptide, both said first and second polypeptides containing a C and an N terminus, comprising the steps of:
   (1) selecting, using computer methods, two sites, Tau 1 and Sigma 1, said site Tau 1 being in a domain 1 of said first polypeptide, and said site Sigma 1 being in a domain 2 of said second polypeptide;
   (2) selecting, using computer methods, a site, Tau 2, in said domain 1 of said first polypeptide, said site Tau 2 being before Tau 1 in said domain 1 of said first polypeptide;
   (3) selecting, using computer methods, a site, Sigma 2, in said domain 2 of said second polypeptide, said site Sigma 2 being before Sigma 1 in said domain 2 of said polypeptide, where Sigma 1 is near the C terminus;
   (4) picking a first possible linker from a computer data base for linking said sites Tau 1 and Sigma 1 to one another;
   (5) picking a second possible linker from a computer data base for linking said sites Tau 2 and Sigma 2 to one another; and
   (6) visually displaying, using computer graphics, at least a portion of computer-designed protein molecules from steps 1-5.

* * * * *